United States Patent [19]
Cox et al.

[11] Patent Number: 5,747,496
[45] Date of Patent: May 5, 1998

[54] INHIBITORS OF PLATELET AGGREGATION

[75] Inventors: David Cox; Anthony Ingall, both of Loughborough; Paul Willis, West Bridgford, all of England

[73] Assignee: Astra Pharmaceuticals Limited, Herts, England

[21] Appl. No.: 737,005

[22] PCT Filed: Jul. 4, 1996

[86] PCT No.: PCT/SE96/00911

§ 371 Date: Oct. 31, 1996

§ 102(e) Date: Oct. 31, 1996

[87] PCT Pub. No.: WO97/03084

PCT Pub. Date: Jan. 30, 1997

[30] Foreign Application Priority Data

Jul. 11, 1995 [GB] United Kingdom ............... 9514074
Oct. 5, 1995 [GB] United Kingdom ............... 9520311
Nov. 8, 1995 [GB] United Kingdom ............... 9522837

[51] Int. Cl.⁶ .................. C07H 19/16; C07D 487/04; C07D 403/04; A61K 31/505
[52] U.S. Cl. ........................................ 514/258; 544/254
[58] Field of Search ........................ 544/254; 514/258

[56] References Cited

U.S. PATENT DOCUMENTS

| | | | |
|---|---|---|---|
| 5,039,689 | 8/1991 | Daluge | 514/359 |
| 5,506,347 | 4/1996 | Erion et al. | 536/4.1 |

FOREIGN PATENT DOCUMENTS

| | | |
|---|---|---|
| 0 215 759 | 3/1987 | European Pat. Off. |
| 4004558 A1 | 9/1990 | Germany. |
| 2 228 479 | 8/1990 | United Kingdom. |
| 94/17803 | 8/1994 | WIPO. |

*Primary Examiner*—Mukund J. Shah
*Assistant Examiner*—Bruck Kifle
*Attorney, Agent, or Firm*—Nixon & Vanderhye

[57] ABSTRACT

Compounds of the formula (I)

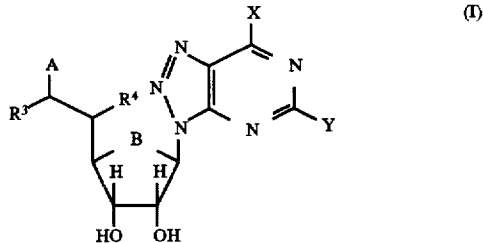

wherein

B is O or $CH_2$;

X is selected from $NR^1R^2$, $SR^1$, and $C_1-C_7$ alkyl;

Y is selected $SR^1$, $NR^1R^2$, and $C_1-C_7$ alkyl;

$R^1$ and $R^2$ is each and independently selected from H, or $C_1-C_7$ alkyl optionally substituted upon or within the alkyl chain by one or more of O, S, N or halogen;

$R^3$ and $R^4$ are both H, or $R^3$ and $R^4$ together form a bond;

A is COOH, $C(O)NH(CH_2)_p COOH$, $C(O)N[(CH_2)_q COOH]_2$, $C(O)NHCH(COOH)(CH_2)_r COOH$, or 5-tetrazolyl, wherein p, q and r is each and independently 1, 2 or 3;

as well as pharmaceutically acceptable salts and prodrugs thereof, pharmaceutical compositions comprising the novel compounds and use of the compounds in therapy. Also within the scope of the invention are novel intermediates to the novel compounds. The novel compounds are in particular useful in the prevention of platelet aggregation.

19 Claims, No Drawings ic
INHIBITORS OF PLATELET AGGREGATION

FIELD OF THE INVENTION

The present invention is directed to novel compounds, to a process for their preparation, their use and pharmaceutical compositions comprising the novel compounds. The novel compounds are useful in therapy, and in particular in the prevention of platelet aggregation.

BACKGROUND AND PRIOR ART

A number of converging pathways lead to platelet aggregation. Whatever the initial stimulus, the final common event is a cross linking of platelets by binding of fibrinogen to a membrane binding site, glycoprotein IIb/IIIa (GPIIb/IIIa). The high anti-platelet efficacy of antibodies or antagonists for GPIIb/IIIa is explained by their interference with this final is common event. However, this efficacy may also explain the bleeding problems that have been observed with this class of agent.

Thrombin can produce platelet aggregation largely independently of other pathways but substantial quantities of thrombin are unlikely to be present without prior activation of platelets by other mechanisms. Thrombin inhibitors such as hirudin are highly effective anti-thrombotic agents, but again may produce excessive bleeding because they function as both anti-platelet and anti-coagulant agents (The TIMI 9a Investigators (1994), *Circulation* 90, pp. 1624–1630; The Global Use of Strategies to Open Occluded Coronary Arteries (GUSTO) IIa Investigators (1994) *Circulation* 90, pp. 1631–1637; Neuhaus K. L. et. al. (1994) *Circulation* 90, pp. 1638–1642).

Aspirin, which is known to have a beneficial effect on platelet aggregation, (see e.g. Antiplatelet Trialists' Collaboration (1994), *Br. Med. J.* 308, pp. 81–106; Antiplatelet Trialists' Collaboration (1994), *Br. Med. J.* 308, pp. 159–168) has no effect on aggregation produced by other sources of ADP, such as damaged cells or ADP released under conditions of turbulent blood flow. A pivotal role for ADP is supported by the fact that other agents, such as adrenaline and 5-hydroxytryptamine (5HT, serotonin) will only produce aggregation in the presence of ADP.

The inventors of the present invention started from the point that an antagonist of the effect of ADP on its platelet membrane receptor, the $P_{2T}$-purinoceptor, would provide a more efficacious anti-thrombotic agent than aspirin but with less profound effects on bleeding than antagonists of the fibrinogen receptor.

U.S. Pat. No. 4,543,255 discloses carbocyclic analogues of 2-amino-6-substituted purine 2'-deoxyribofuranosides and of 2-amino-6-substituted-8-azapurine 2'-deoxyribofuranosides. The compounds of this prior art patent are disclosed as having inhibitory effect against herpes viruses.

WO 90/06671 discloses the use of carbocyclic analogues of various nucleosides for the treatment of Hepatitis B virus.

The problem underlying the present invention was to find novel compounds having improved $P_{2T}$-receptor antagonist activity and with significant advantages with respect to known anti-platelet agents, such as improved efficacy, reduced side-effects, non-toxicity, and better selectivity for the $P_{2T}$-receptor.

The problem mentioned above has now been solved by providing novel compounds which are 5,7-disubstituted 1,2,3-triazolo[4,5-d]pyrimidin-3-yl derivatives, as will be described below.

OUTLINE OF THE INVENTION

The novel compounds according to the present invention are defined by the general formula (I)

$$\text{(I)}$$

wherein

B is O or $CH_2$;

X is selected from $NR^1R^2$, $SR^1$, and $C_1$–$C_7$ alkyl;

Y is selected from $SR^1$, $NR^1R^2$, and $C_1$–$C_7$ alkyl;

$R^1$ and $R^2$ is each and independently selected from H, or $C_1$–$C_7$ alkyl optionally substituted upon or within the alkyl chain by one or more of O, S, N or halogen;

$R^3$ and $R^4$ are both H, or $R^3$ and $R^4$ together form a bond;

A is COOH, $C(O)NH(CH_2)_p COOH$, $C(O)N[(CH_2)_q COOH]_2$, $C(O)NHCH(COOH)(CH_2)_r COOH$, or 5-tetrazolyl, wherein p, q and r is each and independently 1, 2 or 3;

The definition of alkyl is intended to include straight, branched, and cyclic alkyl chains, as well as saturated and unsaturated alkyl chains.

The O, S and N substituents may be substituents upon or within the alkyl chain. By this definition we mean $C_1$–$C_7$ alkyl where one methylene within the chain may optionally be replaced by O, S or NH and in which the alkyl chain may be optionally substituted by one or more of OH, SH, $NH_2$ or halogen.

Halogen includes chloro and fluoro.

Within the scope of the invention are also pharmaceutically acceptable salts of the compounds of the formula (I), as well as prodrugs such as esters and amides thereof.

Also within the scope of the invention are compounds of the formula (I) in tautomeric, enantiomeric and diastereomeric forms.

Preferred compounds of the invention are compounds of the formula (I) wherein

X is $NR^1R^2$;

Y is $SR^1$;

A is $C(O)NHCH(COOH)(CH_2)_r COOH$;

and wherein $R^1$, $R^2$, and r are as defined above.

Especially preferred compounds of the invention are compounds of the formula (I) wherein X is $NR^1R^2$ wherein $R^1$ is hydrogen and $R^2$ is as defined above;

Y is $SR^1$ where $R^1$ is $C_1$–$C_5$ alkyl optionally substituted by one or more halogens; and A is $C(O)NHCH(COOH)CH_2COOH$ The most preferred compounds of the invention are (E)-N-[1-[7-(Butylamino)-5-(propylthio)-3H-1,2,3-triazolo[4,5-d]pyrimidin-3-yl]-1,5,6-trideoxy-β-D-ribo-hept-5-enofuranuronoyl]-L-aspartic acid;

[1R-(1α,2β,3β,4α)]-N-[3-[4-[7-(Butylamino)-5-(propylthio)-3H-1,2,3-triazolo[4,5-d]pyrimidin-3-yl]-2,3-dihydroxycyclopentyl]propanoyl]-L-aspartic acid;

[1R-(1α(E),2β,3β,4α)]-N-[3-[4-[7-(Hexylamino)-5-(propylthio)-3H-1,2,3-triazolo[4,5-d]pyrimidin-3-yl]-2,3-dihydroxycyclopentyl]-2-propenoyl]-L-aspartic acid; and

[1R-(1α(E),2β,3β,4α)]-N-[3-[4-[5-[(3,3,3-Trifluoropropyl)
thio]-7[2-(methylthio)ethylamino]-3H-1,2,3-triazolo[4,5-
d]pyrimidin-3-yl]-2,3-dihydroxycyclopentyl]-2-
propenoyl]-L-aspartic acid, monoammonium salt.

The novel compounds of the present invention are useful in therapy, in particular in the prevention of platelet aggregation. The compounds of the present invention are thus useful as anti-thrombotic agents, and are thus useful in the treatment or prophylaxis of unstable angina, coronary angioplasty (PTCA), and myocardial infarction.

The compounds of the present invention are also useful in the treatment or prophylaxis of primary arterial thrombotic complications of atherosclerosis such as thrombotic stroke, peripheral vascular disease, myocardial infarction (i.e. without thrombolysis).

Still further indications where the compounds of the invention are useful are for the treatment or prophylaxis of arterial thrombotic complications due to interventions in atherosclerotic disease such as angioplasty, endarterectomy, stent placement, coronary and other vascular graft surgery.

Still further indications where the compounds of the invention are useful are for the treatment or prophylaxis of thrombotic complications of surgical or mechanical damage such as tissue salvage following surgical or accidental trauma, reconstructive surgery including skin flaps, and "reductive" surgery such as breast reduction.

The compounds of the invention are also useful for the prevention of mechanically-induced platelet activation in vivo, such as cardio-pulmonary bypass (prevention of microthromboembolism), prevention of mechanically-induced platelet activation in vitro such as the use of the compounds in the preservation of blood products, e.g. platelet concentrates, prevention of shunt occlusion such as renal dialysis and plasmapheresis, thrombosis secondary to vascular damage/inflammation such as vasculitis, arteritis, glomerulonephritis, and organ graft rejection.

Still further indication where the compounds of the present invention are useful are indications with a diffuse thrombotic/platelet consumption component such as disseminated intravascular coagulation, thrombotic thrombocytopenic, purpura, haemolytic uraemic syndrome, thrombotic complications of septicaemia, adult respiratory distress syndrome, anti-phosholipid syndrome, heparin-induced thrombocytopaenia and pre-eclampsia/eclampsia.

Still further indications where the compounds of the invention are useful are for the treatment or prophylaxis of venous thrombosis such as deep vein thrombosis, veno-occlusive disease, haematological conditions such as thrombocythaemia and polycythaemia, and migraine.

In a particularly preferred embodiment of the present invention, the compounds are used in the treatment of unstable angina, coronary angioplasty and myocardial infarction.

In another particularly preferred embodiment of the invention, the compounds of the present invention are useful as adjunctive therapy in the prevention of coronary arterial thrombosis during the management of unstable angina, coronary angioplasty and acute myocardial infarction, i.e. perithrombolysis. Agents commonly used for adjunctive therapy in the treatment of thrombotic disorders may be used, for example heparin and/or aspirin, just to mention some.

METHODS OF PREPARATION

The compounds of the present invention may be prepared as follows.

A)

(i) The starting material 4,5-diamino-2,6-dimercaptopyrimidine is subjected to an alkylation reaction followed by diazotization, giving a compound of the formula (II)

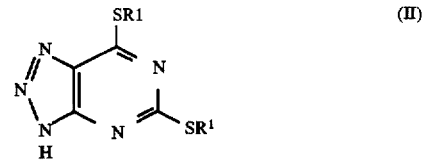

wherein $R^1$ is as defined in formula (I).

(ii) The product of the formula (11) of step (i) is reacted with a compound of the formula (III)

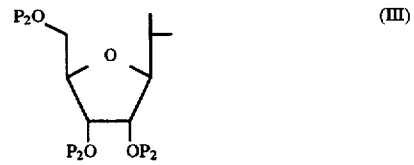

wherein
$P_2$ is protecting group; and
L is a leaving group;
in an inert solvent and in the presence of a base. Solvents which may be used include DMF, and bases which may be used include sodamide. The reaction is carried out at temperatures from −20° to 50° C. Preferably the reaction is carried out at ambient temperature, the solvent is acetonitrile and the base sodium hydride. A suitable protecting group includes an acyl group such as benzoyl, and a suitable leaving group includes a halogen such as bromine.

The reagent of formula (III) used in this step, is prepared by the halogenation of a suitably protected ribose.

Thereafter the group $X=NR^1R^2$ wherein $R^1$ and $R^2$ are as defined in formula (I) above may be introduced by reaction with a compound of the formula $HNR^1R^2$ wherein $R^1$ and $R^2$ are as defined in formula (I) above, in an inert solvent at temperatures from 0° to 150°. Preferably the solvent is 1,4-dioxane and the temperature 100° C.

The protecting groups $P_2$ may be removed by treatment with a nucleophile, for example an alkoxide in an alcohol solvent, preferably sodium methoxide in methanol at 60° C.

The product achieved in this step is a compound of the formula (IV)

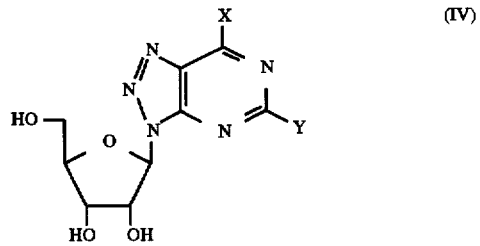

wherein
X is $NR^1R^2$;
Y is $SR^1$; and wherein
$R^1$ and $R^2$ are as defined in formula (I) above.

(iii) The product formula (IV) of step (ii), is reacted with a suitable carbonyl compound or with an ortho ester in an inert solvent and in the presence of a mineral or organic acid catalyst at a temperature between −15° and 100°, giving a compound of the formula (V)

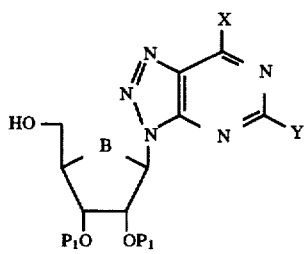

(V)

wherein

X is $NR^1R^2$;

Y is $SR^1$;

B is O; and $P_1$ is a protecting group, preferably $P_1/P_1$ together form a ring.

Preferably $P_1/P_1$ is ethoxymethylidene, introduced using triethyl orthoformate in 1,4-dioxane at 50° C. and in the presence of trichloroacetic acid.

B)

(i) 4,6-dihydroxy-2-mercaptopyrimidine is alkylated followed by nitration, whereafter the two alcohols are converted to leaving groups, giving a compound of the formula (VI)

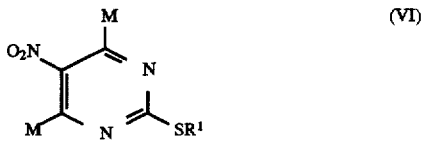

(VI)

wherein is $R^1$ is as defined in formula (I); and

M is a leaving group;

Examples of leaving groups that may be used are halogens.

The compound of formula (VI) is reacted with a suitably protected 5,6-dihydroxy-2-azabicyclo[2.2.1]heptan-3-one, preferably [3aS-(3aα,4β,7β,7aα]-tetrahydro-2,2-dimethyl-4,7-methano-1,3-dioxolo[4,5-c]pyridin-6(3aH)-one, in the presence of a base such as butyl-lithium in an inert solvent such as tetrahydrofuran at temperatures of 10° C. to 100° C., giving a compound of the formula (VII)

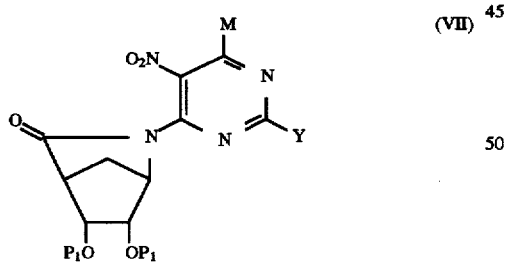

(VII)

wherein

Y is $SR^1$;

$R^1$ is as defined in formula (I);

M is a leaving group; and $P_1$ is a protecting group.

Preferably $P_1/P_1$ together form a ring such as isopropylidene, and preferably the leaving group is chlorine.

Preferably the base is sodium hydride, the solvent DMF and the reaction carried out at ambient temperature.

(ii) The nitro function and the lactam in the product of the formula (VII) of step (i) is reduced, followed by cyclization to a triazole.

Methods of reduction of the nitro group which may be mentioned include hydrogenation using transition metal catalysts such as palladium on charcoal under an atmosphere of hydrogen, at a pressure of 1–5 Bar, in a suitable solvent eg ethanol. Preferably iron in an acidic solvent is used, such as acetic acid at temperatures between 20° and 150° C., most preferred is a temperature of 100° C.

Methods of reduction of the lactam which may be mentioned include the use of complex metal hydrides such as lithium aluminium hydride in an inert solvent such as tetrahydrofuran, at temperatures of 0° to 100° C. Preferably sodium borohydride in methanol is used at temperatures of 0° to 30°.

The diamino alcohol thereby formed is cyclised by a diazotization reaction using metal nitrites or alkyl nitrites in a suitable solvent, for example use of sodium nitrite in dilute aqueous HCl at temperatures of –20° to 100° C. Preferably isoamyl nitrite in acetonitrile is used at 80° C.

The group $X=NR^1R^2$ is introduced by reaction with a compound of formula $HNR^1R^2$ in an inert solvent at temperatures from 0° to 150° C., giving a compound of the formula (V) wherein X is $NR^1R^2$;

Y is $SR^1$;

$R^1$ and $R^2$ are as defined in formula (I);

B is $CH_2$; and $P_1$ is a protecting group.

Preferably 1,4-dioxane is used as the solvent, and the reaction performed at a temperature of 100° C. Preferably $P_1/P_1$ together form a ring, where $P_1/P_1$ being isopropylidene is most preferred.

C)

(i) The product of step A) and B), i.e. a compound of the formula (V) achieved in step A) and B) respectively, is oxidised and subjected to an olefination reaction, giving a compound of the formula (VIII)

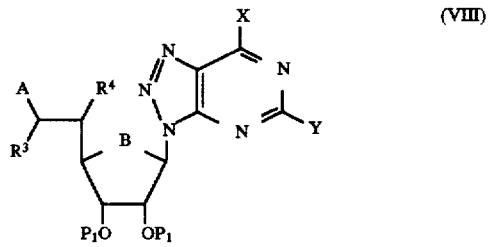

(VIII)

wherein

B is O or $CH_2$;

X, Y and $P_1$ are as defined in formula (V) of step A) and B) respectively;

A is $COOR^{11}$ wherein $R^{11}$ is a lower (ar)alkyl; and $R^3$ and R together form a bond.

Methods of oxidation which may be mentioned include the Swern reaction and use of the Dess Martin reagent, in appropriate solvents at temperatures between –78° and 120° C. Preferably the Pfitzner-Moffatt oxidation in DMSO as solvent is used at ambient temperature, and the protecting groups $P_1/P_1$ together form a ring, most preferred is the case where $P_1/P_1$ is isopropylidene. Methods of olefination which may be mentioned include the Peterson reaction and the Horner Emmons reaction. Preferably a Wittig reaction is used with a phosphorus ylide such as a (carboalkoxymethylene)triphenylphosphorane, particularly preferred is (t-Butoxycarbonylmethylene) triphenylphosphorane.

(ii) $R^{11}$ is removed by de-esterification using acidic or basic or hydrogenolytic conditions, and deprotection is finally performed, giving a compound of the formula (I) wherein X is $NR^1R^2$;

Y is $SR^1$;

B is O or $CH_2$;

$R^1$ and $R^2$ are as defined in formula (I);

$R^3$ and $R^4$ together form a bond; and

A is COOH.

Groups $R^{11}$ which may be mentioned include methyl, ethyl, isopropyl, t-butyl and benzyl. Groups $R^{11}$ may be removed by hydrolysis using acid or basic conditions. Basic hydrolysis may be performed using metal hydroxides or quaternary ammonium hydroxides such as sodium hydroxide in a solvent such as aqueous ethanol at a temperature between −10° and 100°. We prefer lithium hydroxide in aqueous tetrahydrofuran at ambient temperature. Acidic hydrolysis may be performed using mineral acid such as HCl or strong organic acid such as trifluoroacetic acid in a suitable solvent eg aqueous 1,4-dioxane. Benzyl groups may be removed by hydrogenolysis using transition metal catalysts eg palladium on charcoal under an atmosphere of hydrogen, at a pressure between 1 and 5 Bar, in a suitable solvent such as acetic acid. We prefer $R^{11}$=t-Butyl and hydrolysis using trifluoroacetic acid in dichloromethane.

The protecting groups in the case of acyl and benzyl may be removed as described for $R^{11}$ above, silyl protecting groups may be removed by the use of e.g. fluoride ion. Lower alkyl groups may be removed by the use of for example boron tribromide. Methylidene and ethoxymethylidene may be removed by the use of for example mineral or organic acid. All these methods may be performed at a temperature of between −80° C. and 150° C. Preferably $R^{11}$ is t-butyl and $P_1/P_1$ are isopropylidene both of which are simultaneously removed using trifluoroacetic acid in dichloromethane at ambient temperature.

D)

(i) A compound of the formula (I) wherein

X is $SR^1$, $NR^1R^2$, or $C_1$–$C_7$ alkyl;

Y is $SR^1$, $NR^1R^2$, $C_1$–$C_7$ alkyl;

$R^1$ and $R^2$ are as defined in formula (I);

B is O or $CH_2$;

$R^3$ and $R^4$ are hydrogen or together form a bond; and

A is COOH;

is reacted with a compound having the structure $NH_2(CH_2)_pCOOR^{11}$, $NH[(CH_2)_qCOOR^{11}]_2$, or $NH_2CH(COOR^{11})(CH_2)_rCOOR^{11}$, wherein p, q and r are 1, 2 or 3, and $R^{11}$ is a lower (ar)alkyl;

using methods as employed in peptide synthesis, e.g. the use of a coupling agent. Coupling, agents which may be used include 1,1'-carbonyldiimidazole, N-ethoxycarbonyl-2-ethoxy-1,2-dihydroquinoline.

A compound of the formula (I) wherein

X is $SR^1$, $NR^1R^2$, or $C_1$–$C_7$ alkyl;

Y is $SR^1$, $NR^1R^2$; $C_1$–$C_7$ alkyl;

B is O or $CH_2$;

$R^3$ and $R^4$ are hydrogen or together form a bond; and

A is $C(O)NH(CH_2)_pCOOR^{11}$, $C(O)N[(CH_2)_qCOOR^{11}]_2$, or $C(O)NHCH(COOR^{11})(CH_2)_rCOOR^{11}$ where p, q and r are 1, 2 or 3, and $R^{11}$ is a lower (ar)alkyl.

is achieved in this step.

Groups $R^{11}$ which may be mentioned include methyl, ethyl, isopropyl, t-butyl and benzyl. The coupling reaction is carried out in a suitable solvent at a temperature between −15° C. and 120° C. Preferably dicyclohexylcarbodiimide or bromo-tris-pyrrolidinophosphonium hexafluorophosphate in N,N-Dimethylformamide (DMF) is used at a temperature between 0° C. and room temperature.

(ii) The product of formula (I) of step (i) is de-esterified, giving a compound of the formula (I) wherein B is O or $CH_2$;

X is $NR^1R^2$, $SR^1$, or $C_1$–$C_7$ alkyl;

Y is $SR^1$, $NR^1R^2$, or $C_1$–$C_7$ alkyl;

$R^1$ and $R^2$ is each and independently H, or $C_1$–$C_7$ alkyl optionally substituted upon or within the alkyl chain by one or more of O, S, N or halogen;

$R^3$ and $R^4$ are both H, or $R^3$ and $R^4$ together form a bond; and

A is $C(O)NH(CH_2)_pCOOH$, $C(O)N[(CH_2)_qCOOH]_2$, or $C(O)NHCH(COOH)(CH_2)_rCOOH$, wherein p, q and r is each and independently 1, 2 or 3.

Groups $R^{11}$ which may be mentioned include methyl, ethyl, isopropyl, t-butyl and benzyl. Groups $R^{11}$ may be removed by hydrolysis using acid or basic conditions. Basic hydrolysis may be performed using metal hydroxides or quaternary ammonium hydroxide such as sodium hydroxide in a solvent such as aqueous ethanol at a temperature between 10° and 100°. We prefer lithium hydroxide in aqueous tetrahydrofuran at ambient temperature. Acidic hydrolysis may be performed using mineral acid such as HCl or strong organic acid such as trifluoroacetic acid in a suitable solvent eg aqueous 1,4-dioxane. Benzyl groups may be removed by hydrogenolysis using transition metal catalysts eg, palladium on charcoal under an atmosphere of hydrogen, at a pressure between 1 and 5 Bar, in a suitable solvent such as acetic acid. We prefer $R^{11}$=t-Butyl and hydrolysis using trifluoroacetic acid in dichloromethane.

E)

(i) The product achieved in step C(ii) is reduced, giving a compound of the formula (I) wherein B, X, Y, $R^1$ and $R^2$ are as defined in step C(ii) above;

A is COOH; and $R^3$ and $R^4$ are both hydrogen.

Methods of reduction which may be used include hydrogenation using transition metal catalysts, for example palladium on charcoal under an atmosphere of hydrogen in a suitable solvent such as acetic acid at a pressure of 1 to 5 bar. Preferably diimide generated from a suitable precursor such as 2,4,6-triisopropylbenzene sulfonylhydrazide is used at a temperature between 60° and 100° C., in a solvent of tetrahydrofuran (THF).

F)

(i) A suitably protected 5-amino-1-(β-D-ribo-furanosyl)-1,2,3-triazole-4-carboxamide, preferably 5-Amino-1-[2,3-O-(1-methylethylidene)-β-D-ribo-furanosyl]-1,2,3-triazole-4-carboxamide is treated with a base followed by treatment with an ester having the formula $R^1COOR^5$ where $R^1$ is as defined in structure (I) and $R^5$ is a lower alkyl. Thereafter protection is performed, giving a compound of the formula (IX)

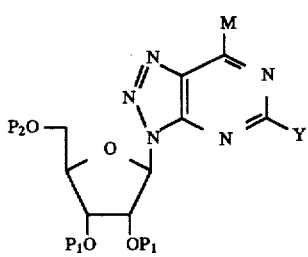

(IX)

wherein

Y is $C_1$–$C_7$ alkyl;

$P_1$ is a protecting group, and preferably $P_1/P_1$ together form a ring;

$P_2$ is a protecting group; and

M is OH.

Protecting groups $P_2$ which may be mentioned include lower alkyl or acyl groups. Preferably $P_2$ is acetyl, introduced by the treatment with acetyl chloride and triethylamine in a suitable solvent, e.g. dichloromethane at ambient temperature. Most preferably $P_1/P_1$ is isopropylidene and $P_2$ is acetyl.

(ii) The compound of the formula (IX) where M is OH, is halogenated and the group X=$NR^1R^2$ is introduced by treatment with a compound of formula $HNR^1R^2$ in an inert solvent at temperatures from 0° to 150°. Thereafter the protecting group $P_2$ is removed, giving a compound of the formula (V) wherein X is $NR^1R^2$;

$R^1$ and $R^2$ are as defined in formula (I);

Y is $C_1$–$C_7$ alkyl;

B is O; and $P_1$ is a protecting group, and preferably $P_1/P_1$ together form a ring. Most preferred is the case where $P_1/P_1$ is isopropylidene.

Halogenating agents which may be mentioned include P(III) or P(V), or S(II) or S(IV) halides such as phosphorous trichloride at temperatures of 0° to 150°. The reactions may be performed in the halogenating agent as solvent or other inert solvents such as methylene chloride. We prefer thionyl chloride in DMF/chloroform at reflux.

A preferred solvent used for the introduction of the group X=$NR^1R^2$ is 1,4-dioxane at a temperature of 100°. Protecting group $P_2$ may be removed under these conditions. Alternatively it may be removed using acidic or basic hydrolytic methods.

Preferably ammonia in methanol is used at ambient temperature.

(iii) The product of formula (V) of step (ii) is subjected to the same reactions as described in steps C(i) and (ii), giving a compound of the formula (I) wherein X is $NR^1R^2$;

$R^1$ and $R^2$ are as defined in formula (I);

B is O;

Y is $C_1$–$C_7$ alkyl;

A is COOH; and $R^3$ and $R^4$ together form a bond.

G)

(i) A suitable protecting group $P_3$ was introduced into a protected 5-amino-1-(β-D-ribo-furanosyl)-1,2,3-triazole-4-carboxamide, preferably 5-amino-1-[2,3-O-(1-methylethylidene)-β-D-ribo-furanosyl]-1,2,3-triazole-4-carboxamide. The resulting intermediate was treated with a base, preferably sodium hydride, followed by treatment with a reagent of the formula

where L is a leaving group, preferably imidazolyl, giving a compound of the formula (X)

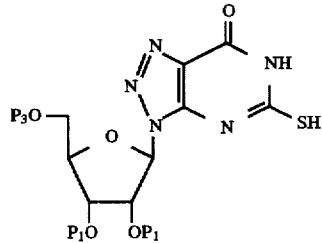

(X)

wherein $P_1$ is a protecting group, preferably where $P_1/P_1$ together form a ring; and $P_3$ is a protecting group, preferably a silyl group.

Most preferred is the case where $P_1/P_1$ is isopropylidene and $P_3$ is t-butyldimethylsilyl.

(ii) The product of formula (X) of step (i) was treated with a base such as butyl lithium in an inert solvent such as THF at a temperature between −20° C. and 50° C., followed by treatment with an alkylating agent $R^1G$ where G is a leaving group, such as a halogen, and wherein $R^1$ is as defined in formula (I).

Preferably sodium hydride is used as a base, in DMF at ambient temperature, and G is iodine.

Thereafter $P_3$ was removed from the above compound, and replaced with a new protecting group $P_2$. Preferably $P_2$ is an acyl group.

Preferably $P_3$ is a silyl group, removed by treatment with fluoride ion, and replaced with an acyl group. Most preferred is $P_3$ being a t-butyldimethylsilyl group, removed by reaction with tetra-n-butylammonium fluoride in THF followed by introduction of a protecting group $P_2$ by reaction with acetyl chloride in dichloromethane at ambient temperature.

Halogenation is finally performed, giving a compound of the formula (IX)

wherein

M is a leaving group, for example a halogen and preferably chlorine;

$P_1$ is a protecting group, preferably $P_1/P_1$ together form a ring; and $P_2$ is a protecting group, preferably acetyl; and Y is $SR^1$.

Halogenating agents which may be mentioned include P(III) or P(V), or S(II) or S(IV) halides such as phosphorous trichloride at temperatures of 0° C. to 150° C. The reactions may be performed in the halogenating agent as solvent or other inert solvents such as methylene chloride. Preferably thionyl chloride in DMF/chloroform is used at reflux.

(iii) The product of step (ii) was reacted with an alkyl nucleophile, eg. a Grignard reagent in an inert solvent such as THF at a temperature between −20° C. and 150° C. Preferably the alkyl nucleophile is an alkyltin species used in the presence of a Pd(II) catalyst. Thereafter the protecting group $P_2$ was removed, giving a compound of the formula (V) wherein X is $C_1$–$C_7$ alkyl;

Y is $SR^1$;

$R^1$ is as defined for formula (I);

B is O; and $P_1$ is a protecting group, preferably where $P_1/P_1$ together form a ring, which most preferably is isopropylidene.

The protecting group $P_2$ may be removed by acidic or basic hydrolytic methods. Preferably $P_2$ is acetyl, removed by the treatment with ammonia in methanol at ambient temperature.

H)
(i) A compound of the formula (I) wherein

X is $NR^1R^2$;

Y is $SR^1$;

$R^1$ and $R^2$ are as defined in formula (I);

B is O;

$R^3$ and $R^4$ are both hydrogen; and

A is $C(O)NHCH(COOR^{11})(CH_2)_rCOOR^{11}$, where r is 1, 2 or 3, and $R^{11}$ is as defined above;

was treated with an oxidant such as magnesium monoperoxyphthalate in an inert solvent such as THF at temperature between –20° C. and 100° C., followed by treatment with a compound of the formula $HNR^1R^2$ in an inert solvent at temperatures from 0° C. to 150 C., giving a compound of the formula (I) wherein X is $NR^1R^2$;

Y is $NR^1R^2$;

B is O;

$R^3$ and $R^4$ are both hydrogen; and

A is $C(O)NHCH(COOR^{11})(CH_2)_rCOOR^{11}$, where r is 1, 2 or 3, and $R^{11}$ is as defined in step D) above.

Preferably m-chloroperoxybenzoic acid is used as an oxidant in a solvent of ethanol at ambient temperature, and the displacement is carried out in 1,4-dioxane at 100° C.

I) A compound of the formula (I) wherein

X is $SR^1$

Y is $SR^1$;

B is O;

$R^3$ and $R^4$ are both hydrogen; and

A is COOH;

may be prepared by reacting a compound of the formula (II) wherein $R^1$ is as defined in formula (I), with a compound of the formula (XI)

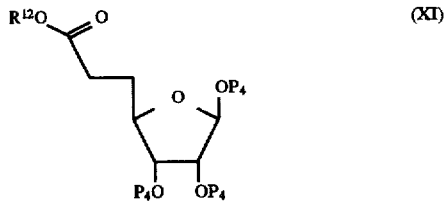

(XI)

wherein $R^{12}$ is a lower (ar)alkyl and $P_4$ is a protecting group such as an acetyl group.

The reaction may be carried out by heating the compounds together in the presence of an acid such as trichloroacetic acid at reduced pressure and at a temperature between 50° and 175° C. Preferably $R^{12}$ is ethyl, $P_4$ is acetyl and the reaction is carried out at 140° C. in the presence of p-toluenesulfonic acid under water pump vacuum.

The protecting groups and the group $R^{12}$ may then be removed by hydrolysis under acidic or basic conditions, giving a compound of the formula (I) wherein X is $SR^1$ Y is $SR^1$;

$R^1$ is as defined for formula (I);

B is O;

$R^3$ and $R^4$ are both hydrogen; and

A is COOH;

Examples of hydrolyzing agents and conditions that may be used, are metal alkoxides in alcohol at temperatures between 0° and 100° C., or alternatively trifluoroacetic acid in dichloromethane may be used. Preferably $R^{12}$ is ethyl and $P_4$ is acetyl, and lithium hydroxide in aqueous tetrahydrofuran is used at ambient temperature.

A compound of the formula (XI) which is one of the starting materials in this reaction step, is initially prepared from (E)-Methyl 5,6-dideoxy-2,3-O-(1-methylethylidene)-β-D-ribo-hept-5-enofuranosiduronic acid, ethyl ester by hydrolysis with an aqueous acid, eg aqueous acetic acid and reaction with an acylating agent such as acetyl chloride in the presence of a base eg pyridine and a suitable solvent eg methylene chloride, followed by reduction, e.g. hydrogenation using transition metal catalysts such as palladium on carbon under atmosphere of hydrogen in a suitable solvent, e.g. ethanol at a pressure between 1 and 3 bar.

J) A compound of the formula (I) wherein

X is $NR^1R^2$;

Y i $SR^1$;

$R^1$ and $R^2$ are as defined in formula (I);

B is O or $CH_2$;

$R^3$ and $R^4$ are both hydrogen; and

A is 5-tetrazolyl;

was prepared as follows.

The product in step A(iii) or the product of step B(ii), i.e. a compound of the formula (V) wherein B is O or $CH_2$ and X and Y are as defined in formula (V) above, and $P_1$ is a protecting group, preferably where $P_1/P_1$ together form a ring, was oxidised followed by an olefination reaction and a subsequent reduction.

Methods of oxidation which may be mentioned include the Swern reaction and use of the Dess Martin reagent in appropriate solvents at temperatures between –78° and 120° C. Preferably the Pfitzner-Moffatt oxidation was performed in a solvent of DMSO at ambient temperature using a compound of the formula (V) wherein $P_1/P_1$ is isopropylidene. Methods of olefination which may be mentioned include the Peterson reaction and the Horner Emmons reaction. We prefer a Wittig reaction with the phosphorus ylid (triphenylphosphoranylidene)acetonitrile. Methods of reduction which may be mentioned include hydrogenation using transition metal catalysts such as platinum under an atmosphere of hydrogen in a suitable solvent eg acetic acid at temperatures between 0° and 100°. We prefer palladium on charcoal under a pressure of 4 Bar in a solvent of ethanol at ambient temperature.

The product thus achieved was a compound of the formula (XIII)

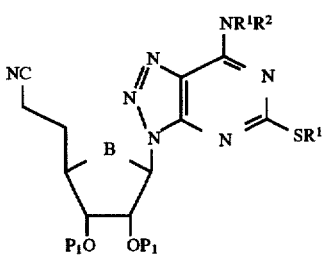

wherein

B is O or CH₂;

P₁ is a protecting group, preferably where P₁/P₁ together form a ring and most preferably where P₁/P₁ is isopropylidene; and R¹ and R² are as defined in formula (I).

This compound of the formula (XII) was reacted with an azide such as sodium azide in an inert solvent, e.g. DMF, at a temperature between 0° C. and 175° C. Isopropylidene is a preferred protecting group. Preferably tributyltin azide in toluene is used at a temperature of 110° C.

The protecting groups are thereafter removed by treatment with a mineral or organic acid in an inert solvent at a temperature between 0° C. and 100° C. Preferably trifluoroacetic acid in dichloromethane is used at ambient temperature.

A product of the formula (I) wherein

X is NR¹ R²;

Y is SR¹;

R¹ and R² are as defined in formula (I);

B is O or CH₂;

R³ and R⁴ are both hydrogen; and

A is 5-tetrazolyl;

was thus achieved.

K)

A compound of the formula (I) wherein

X is SR¹, NR¹R² or $C_1$–$C_7$ alkyl;

Y is SR¹, NR¹R² or $C_1$–$C_7$ alkyl;

R and R² are as defined in formula (I);

B is CH₂ or O;

R³ and R⁴ together form a bond; and

A is COOR¹¹ wherein R¹¹ is as defined in formula (I) above;

is reduced, giving a compound of the formula (VIII) wherein

R³ and R⁴ are hydrogen; and

X, Y, B, A, R¹¹ and Pd₁ are as defined above.

Methods of reduction which may be mentioned include hydrogenation using transition metal catalysts, e.g. palladium on charcoal under an atmosphere of hydrogen in a suitable solvent such as acetic acid at a pressure of 1 to 5 bar. Preferably diimide generated from a suitable precursor such as 2,4,6-triisopropylbenzenesulfonylhydrazide at a temperature between 60° C. and 100° C. is used in a solvent of tetrahydrofuran.

(ii) The product of step (i) is subjected to the same reaction conditions as described in step D(ii), giving a compound of the formula (I) wherein X is SR¹, NR¹R² or $C_1$–$C_7$ alkyl;

Y is SR¹, NR¹R² or $C_1$–$C_7$ alkyl;

R¹ and R² are as defined in formula (I);

B is CH₂ or O; and

A is COOH.

The compounds of the formula (I), as well as salts, and prodrugs such as esters or amides thereof, may be isolated from their reaction mixtures using conventional techniques.

Salts of the compounds of formula (I) may be formed by reacting the free acid, or a salt thereof, or the free base, or a salt or derivative thereof, with one or more equivalents of the appropriate base or acid. The reaction may be carried out in a solvent or medium in which the salt is insoluble or in a solvent in which the salt is soluble, e.g. water, ethanol, tetrahydrofuran or diethyl ether, which may be removed in vacuo, or by freeze drying. The reaction may also be a metathetical process or it may be carried out on an ion exchange resin. The non-toxic physiologically acceptable salts are preferred, although other salts may be useful, e.g. in isolating or purifying the product.

Pharmaceutically acceptable esters of the compounds of formula I may be made by conventional techniques, e.g. esterification or transesterification.

Pharmaceutically acceptable amides of the compounds of formula I may be made by conventional techniques, e.g. reaction of an ester of the corresponding acid with ammonia or an appropriate amine.

DETAILED DESCRIPTION OF THE INVENTION

The invention will now be described in more detail by the following examples, which are not to be construed as limiting the invention.

Temperatures are given in degrees Celsius in the Examples if nothing else has been indicated.

EXAMPLES

Example 1

[1R-(1α(E),2β,3β,4α)-3-[4-[7-(Butylamino)-5-(propylthio)-3H-1,2,3-triazolo[4,5-d]pyrimidin-3-yl]-2,3-dihydroxycyclopentyl]-2-propenoic acid, sodium salt]

a) 2-(Propylthio)-4,6(1H,5H)-pyrimidinedione

Propyl iodide (136 ml) was added to a suspension of 4,6-dihydroxy-2-mercaptopyrimidine (200 g) in water (800 ml), containing sodium hydroxide (55.6 g). The reaction mixture was stirred for 2 weeks then concentrated to half volume, 2N hydrochloric acid added and the product isolated by filtration (167 g).

MS (EI): 186 (M⁺, 100%).

b) 6-Hydroxy-5-nitro-2-(propylthio)-4(1H)-pyrimidinone

The product of step a) (70 g) was added slowly to ice-cooled fuming nitric acid (323 ml). The reaction mixture was stirred for 1 hour then poured onto ice and the product isolated by filtration (65 g).

MS (EI): 231 (M⁺), 41 (100%).

c) 4,6-Dichloro-5-nitro-2-(propylthio)pyrimidine

N,N-Dimethylaniline (150 ml) was added dropwise to a stirred suspension of the product of step b) (134 g) in phosphoryl chloride (500 ml) and the resulting solution heated at reflux for 1 hour. The cooled reaction mixture was poured onto ice then extracted with diethyl ether (3×500 ml). The combined extracts were dried and concentrated. Chromatography (SiO₂, isohexane:diethyl ether, 19:1 as eluant) gave the subtitle compound (128 g).

MS (EI):271, 269, 267 (M⁺), 41 (100%).

d) [3aS-(3aα,4β,7βaα)5-[6-Chloro-5-nitro-2-(propylthio)-pyrimidin-4-yl]-tetrahydro-2,2-dimethyl-4,7-methano-1,3-dioxolo[4,5-c]pyridin-6(3aH)-one Sodium hydride (60%, 4.00 g) was added portionwise to [3aS-(3aα,4β,7β,7aα] tetrahydro-2,2-dimethyl-4,7- methano-1,3-dioxolo[4,5-c]pyridin-6(3aH)-one (18.3 g) in THF (500 ml). On stirring for 1 hr the solution was added dropwise to the product of step c) (54.0 g) in THF (500 ml). The reaction mixture was stirred at r.t for 45 minutes then concentrated and purified by chromatography (SiO$_2$, dichloromethane:isohexane, 3:2 as eluant) to afford the subtitle compound (79.2 g).

MS (APCI) 417, 415 (M+H$^+$), 415 (100%).

e) [3aS-(3aα,4β,7β,7aα)] 5-[5-Amino-6-chloro-2-(propylthio)-pyrimidin-4-yl]-tetrahydro-2,2-dimethyl-4,7-methano-1,3-dioxolo[4,5-c]pyridin-6(3aH)-one Reduced iron powder (50 g) was added to a solution of the product of step d) (50.0 g) in glacial acetic acid (1.8 L) and the reaction mixture heated at reflux for 15 minutes. The cooled reaction mixture was concentrated and the residue taken into ether (2 L) then washed with sodium bicarbonate solution (2×1L). The organic phase was dried and concentrated to afford the sub-title compound (42.6 g).

MS (APCI) 387, 385 (M+H$^+$), 385 (100%).

f) [3aR-(3aα,4α,6α,6aα)]-6-[5-Amino-6-chloro-2-(propylthio)-4-pyrimidinylamino]-tetrahydro-2,2-dimethyl-4H-cyclopenta-1,3-dioxole-4-methanol Sodium borohydride (8.37 g) was added to an ice-cooled solution of the product of step e) (42.6 g) in methanol (1.3L). After stirring for 1 hour the solution was poured into water (2L) and extracted with diethyl ether (2×1L). The combined extracts were dried and concentrated. Purification (SiO$_2$, dichloromethane:ethyl acetate, 1:1 as eluant) gave the subtitle compound (36.1 g).

MS (APCI) 419, 417 (M+H$^+$), 417 (100%).

g) [3aR-(3aα,4α,6α,6aα)]-6-[7-Chloro-5-(propylthio)-3H-1,2,3-triazolo[4,5-d]pyrimidin-3-yl]-tetrahydro-2,2-dimethyl-4H-cyclopenta-1,3-dioxole-4-methanol Isoamyl nitrite (24.9 ml) was added to a solution of the product of step f) (36.0 g) in acetonitrile (80 ml) and the solution heated at 70° for 1 hour. The cooled reaction mixture was concentrated and purified (SiO$_2$, dichloromethane:ethyl acetate, 4:1 as eluant) to afford the subtitle compound (33.6 g).

MS (EI) 401, 399 (M+H$^+$), 43 (100%).

h) [3aR-(3aα,4α,6α,6aα)]-6-]7-(Butylamino)-5-(propylthio)-3H-1,2,3-triazolo]4,5-d]pyrimidin-3-yl]-tetrahydro-2,2-dimethyl-4H-cyclopenta-1,3-dioxole-4-methanol The product from step g) (16.75 g) and n-butylamine (30 ml) in 1,4-dioxane (500 ml) were heated under reflux for 1 h. The reaction mixture was concentrated and the residue purified (SiO$_2$, dichloromethane:ethyl acetate, 4:1 as eluant) to afford the subtitle compound (17.8 g).

MS (APCI) 437 (M+H$^+$, 100%).

i) 3aR-(3aα,4α(E),6α,6aα)]-3-[6-[7-(Butylamino)-5-(propylthio)-3H-1,2,3-triazolo[4,5-d]pyrimidin-3-yl]-tetrahydro-2,2-dimethyl-4H-cyclopenta-1,3-dioxol-4-yl]-2-propenoic acid, 1,1-dimethylethyl ester A stirred solution of the product of step h) (0.5 g), pyridine (0.093 ml) and trifluoroacetic acid (0.048 ml) in DMSO (25 ml) was treated with 1,3-dicyclohexylcarbodiimide (0.72 g) and the mixture stirred at room temperature for 24 hours. (t-Butoxycarbonylmethylene)triphenylphosphorane (0.69 g) was added and the reaction stirred for a further 18 hours. The reaction mixture was cooled to 0°, diluted with ethyl acetate (100 ml) and oxalic acid (0.51 g) added. After 30 min the mixture was filtered and the filtrate washed with saturated sodium bicarbonate solution (100 ml), dried and concentrated. Chromatography (SiO$_2$, hexane:ethyl acetate, 5:1 as eluant) gave the subtitle compound (0.55 g).

MS (FAB): 533 (M+H$^+$, 100%).

j) [1R-(1α(E),2β,3β,4α)-3-[4-[7-(Butylamino)-5-(propylthio)-3H-1,2,3-triazolo[4,5-d]pyrimidin-3-yl]-2,3-dihydroxycyclopentyl]-2-propenoic acid, sodium salt A solution of the product from step i) (0.8 g) in 50% aqueous trifluoroacetic acid (100 ml) was stirred at room temperature for 5 hours. The reaction mixture was concentrated and the product recrystallised from ethyl acetate (30 ml). The free acid was taken into methanol:water (2:3, 30 ml) and applied to a Dowex 50×100 ion exchange resin (sodium form), eluting with water. Lyophilisation gave the title salt as a colourless solid (0.43 g).

NMR δH (d$_6$-DMSO): 6.59 (1H, dd), 5.89 (1H, d), 4.94 (1H, m), 4.45 (1H, t), 4.12 (1H, t), 3.45 (2H, m), 2.83 (3H, m), 2.47 (1H, m), 2.00 (1H, m), 1.5 (4H, m), 1.20 (2H, m), 082 (3H, t), 0.71 (3H, t).

Example 2

[1R-(1α(E),2β,3β,4α)]-N-[3-[4-[7-(Butylamino)-5-(propylthio)-3H-1,2,3-triazolo[4,5-d]pyrimidin-3-yl]-2,3-dihydroxycyclopentyl]-2-propenoyl]-L-aspartic acid, disodium salt a) 1R-(1α(E),2β,3β,4α)-N-[3-[4-[7-(Butylamino)-5-(propylthio)-3H-1,2,3-triazolo[4,5-d]pyrimidin-3-yl]-2,3-dihydroxycyclopentyl]-2-propenoyl]-L-aspartic acid, bis(1,1-dimethylethyl) ester L-Aspartic acid di-tertiary butyl ester hydrochloride (0.46 g) and triethylamine (0.23 ml) were added to a solution of the compound of Example 1 (0.6 g) in DMF (25 ml). 1-Hydroxybenzotriazole (0.22 g) was added and the solution cooled in an ice-bath before adding 1,3-dicyclohexylcarbodiimide (0.34 g). The reaction mixture was stirred at 0° for 30 min then at room temperature for 3 days. After removing the solvent, chromatography (SiO$_2$, chloroform:methanol, 40:1 as eluant) gave the subtitle compound (0.63 g).

MS (FAB): 664 (M+H$^+$), 57 (100%).

b) [1R-(1α(E),2β,3β,4α)-N-[3-[4-[7-(Butylamino)-5-(propylthio)-3H-1,2,3-triazolo[4,5-d]pyrimidin-3-yl]-2,3-dihydroxycyclopentyl]-2-propenoyl]-L-aspartic acid, disodium salt A solution of the product of step a) (0.60 g) in dichloromethane (30 ml) containing trifluoroacetic acid (30 ml) was stirred at room temperature for 2 hours. The solution was concentrated and the residue purified (HPLC Nova-Pak® C18 column, 0.1% aqueous ammonium acetate:methanol 50:50 to 0:100 over 15 mins as eluant) to give the title salt as a colourless solid (0.19 g).

NMR δH (d$_6$-DMSO): 6.74 (1H, dd), 6.12 (1H, d), 5.07 (1H, m), 4.38 (1H, m), 4.05 (1H, t), 3.95 (2H, m), 3.12 (2H, t), 2.85 (1H, m), 2.49 (1H, m), 2.30–2.45 (2H, m), 2.0 (1H, m), 1.75 (2H, m), 1.52 (2H, m), 1.47 (2H, m), 1.0 (3H, t), 0.98 (3H, t).

Example 3

[1S-(1α,2β,3β,4α)-4-[7-(Butylamino)-5-(propylthio)-3H-1,2,3-triazolo-[4,5-d]pyrimidin-3-yl]-2,3-dihydroxy-cyclopentanepropanoic acid, sodium salt a) [1S-(1α(E),2β,3β,4α)]-3-[4-[7-(Butylamino)-5-(propylthio)-3H-1,2,3-triazolo[4,5-d]pyrimidin-3-yl]-2,3-dihydroxycyclopentyl]-2-propenoic acid, ethyl ester A stirred solution of the product of Example 1h) (0.6 g), pyridine (0.112 ml) and trifluoroacetic acid (0.058 ml) in DMSO (25 ml) was treated with 1,3-dicyclohexylcarbodiimide (0.87 g) and the mixture stirred at room temperature for 24 hours. (Carbethoxymethylene)

triphenylphosphorane (0.90 g) was added and the reaction stirred for a further 18 hours. The reaction mixture was cooled to 0°, diluted with ethyl acetate (100 ml) and oxalic acid (0.51 g) added. After 30 min the mixture was filtered and the filtrate washed with saturated sodium bicarbonate solution (100 ml), dried and concentrated. The residue was taken into dichloromethane (50 ml)/trifluoroacetic acid (50 ml) and stirred overnight. The solvent was removed and the residue purified by chromatography (SiO$_2$, dichloromethane:ethyl acetate, 1:1 as eluant) to give the subtitle compound (0.36 g).

MS (FAB): 465 (M+H$^+$, 100%).

b) [1S-(1α,2β,3β,4α)]-4-[7-(Butylamino)-5-(propylthio)-3H-1,2,3-triazolo-[4,5-d]pyrimidin-3-yl]-2,3-dihydroxy-cyclopentanepropanoic acid, ethyl ester 2,4,6-Triisopropylbenzenesulfonohydrazide (0.50 g) was added to a solution of the product of step a) (0.35 g) in dry THF (175 ml) and the resulting solution heated at 70° for 3 hours.

The cooled reaction mixture was purified by chromatography (SiO$_2$, dichloromethane:ethyl acetate, 1:1 as eluant) to give the subtitle compound (0.16 g).

MS (EI): 466 (M$^+$), 43 (100%).

c) [1S-(1α,2β,3β,4α)]-4-[7-(Butylamino)-5-(propylthio)-3H-1,2,3-triazolo-[4,5-d]pyrimidin-3-yl]-2,3-dihydroxy-cyclopentanepropanoic acid, sodium salt Lithium hydroxide monohydrate (14 mg) was added to a solution of the product of step b) (0.16 g) in THF (10 ml)/water (10 ml). The solution was stirred at room temperature for 18 hours before removing the solvent in vacuo. Purification (HPLC Nova-Pak® C.18 column, 0.1% aqueous ammonium acetate:methanol 50:50 to 0:100 over 15 mins as eluant) gave the title acid which was taken into methanol (2 ml) and 1N sodium hydroxide solution (0.28 ml) added. The solution was concentrated to give the title salt (0.13 g).

MS (ESI): 439 (M−Na+H$^+$, 100%).

NMR δH (D$_2$O) 5.07 (1H, m), 4.65 (1H, t), 4.08 (1H, t), 3.49 (2H, t), 3.05 (2H, m), 2.62 (1H, m), 2.36 (2H, m), 2.17 (1H, m), 2.00 (1H, m), 1.70 (2H, m), 1.65 (2H, m), 1.61 (2H, m), 1.40 (2H, m), 1.00 (3H, t), 0.97 (3H, t).

Example 4

[1R-(1α(E),2β,3β,4α)]-3-[4-[7-(Butylamino)-5-(pentylthio)-3H-1,2,3-triazolo[4,5-d]pyrimidin-3-yl]-2,3-dihydroxycyclopentyl]-2-propenoic acid, sodium salt a) 2-(Pentylthio)-4,6(1H,5H)-pyrimidinedione To a solution of 4,6-dihydroxy-2-mercaptopyrimidine (14.4 g) in 2N sodium hydroxide solution (100 ml) was added pentyl iodide (15.6 ml) in ethanol (25 ml) and the resulting reaction mixture stirred at room temperature for four days. The ethanol was removed at reduced pressure and N,N-dimethylformamide (80 ml) and pentyl iodide (1.56 ml) added then the reaction mixture stirred for an additional 16 hours. The solution was made acidic by addition of 2N HCl solution and the aqueous layer decanted. The remaining gum was dissolved in methanol and evaporated to dryness then azeotroped with toluene (×2). The solid was triturated with ether, filtered and dried to give the subtitle compound as a white solid (11.9 g).

MS (EI) 214 (M$^+$), 144 (100%).

b) 6-Hydroxy-5-nitro-2-(pentylthio)-4(1H)-pyrimidinone

Prepared according to the method of Example 1b) using the product of step a).

MS (EI): 259 (M$^+$), 43 (100%).

c) 4,6-Dichloro-5-nitro-2-(pentylthio)-pyrimidine

Prepared according to the method of Example 1c) using the product of step b).

MS (FAB): 295, 297, 299 (M+H$^+$), 41 (100%).

d) [3aS-(3aα,4β,7β,7aα)] 5-[6-Chloro-5-nitro-2-(pentylthio)-pyrimidin-4-yl-tetrahydro-2,2-dimethyl-4,7-methano-1,3-dioxolo[4,5-c]pyridin-6(3aH)-one Prepared according to the method of Example 1d) using the product of step c).

MS (FAB): 445, 443 (M+H$^+$), 443 (100%).

e) [3aS-(3aα,4β,7β,7aα)] 5-Amino-6-chloro-2-(pentylthio)-pyrimidin-4-yl]-tetrahydro-2,2-dimethyl-4,7-methano-1,3-dioxolo[4,5-c]pyridin-6(3aH)-one Prepared according to the method of Example 1e) using the product of step d).

MS (EI): 414, 412 (M$^+$), 412 (100%).

f) [3aR-(3aα,4α,6α,6aα)-6-[5-Amino-6-chloro-2-(pentylthio)-4-pyrimidinylamino]-tetrahydro-2,2-dimethyl-4H-cyclopenta-1,3-dioxole-4-methanol Prepared according to the method of Example 1f) using the product of step e).

MS (EI): 418, 416 (M$^+$), 327 (100%).

g) [3aR-(3aα,4α,6α,6aα)]-6-[7-Chloro-5-(pentylthio)-3H-1,2,3-triazolo-[4,5-d]pyrimidin-3-yl]-tetrahydro-2,2-dimethyl-4H-cyclopenta-1,3-dioxole-4-methanol Prepared according to the method of Example 1g) using the product of step f).

MS (APCI): 430, 428 (M+H$^+$), 338 (100%).

h) [3aR-(3aα,4α,6α,6aα)]-6-[7-(Butylamino)-5-(pentylthio)-3H-1,2,3-triazolo-[4,5-d]pyrimidin-3-yl]-tetrahydro-2,2-dimethyl-4H-cyclopenta-1,3-dioxole-4-methanol Prepared according to the method of Example 1h) using the product of step g).

MS (FAB): 465 (M+H$^+$, 100%).

i) [3aR-(3aα,4α(E),6α,6aα)]-3-[6-7-(Butylamino)-5-(pentylthio)-3H-1,2,3-triazolo[4,5-d]pyrimidin-3-yl]-tetrahydro-2,2-dimethyl-4H-cyclopenta-1,3-dioxol-4-yl]-2-propenoic acid, 1,1-dimethylethyl ester Prepared according to the method of Example 1i) using the product of step h).

MS (FAB): 561 (M+H$^+$), 505 (100%).

j) [1R-(1α(E),2β,3β,4α)]-3-[4-[7-(Butylamino)-5-(pentylthio)-3H-1,2,3-triazolo[4,5-d]pyrimidin-3-yl]-2,3-dihydroxycyclopentyl]-2-propenoic acid, sodium salt Prepared according to the method of Example 1j) using the product of step i).

MS (FAB): 487 (M+Na+H$^+$), 465 (100%).

NMR δH (d$_6$-DMSO) 9.00 (1H, t), 6.43 (1H, dd), 5.70 (1H, d), 4.97 (1H, q), 4.32 (1H, t), 3.87 (1H, t), 3.50–3.47 (2H, m), 3.12–3.04 (2H, m), 2.68 (1H, m), 2.38–2.34 (1H, m), 1.93–1.89 (1H, m), 1.64 (2H, m), 1.62 (2H, m), 1.37–1.30 (6H, m)0.91 (3H, t) 0.87 (3H, t).

Example 5

The following compound was prepared according to the method of Example 4:

[1R-(1α(E),2β,3β,4α)]-3-[4-[7-(Ethylamino)-5-(pentylthio)-3H-1,2,3-triazolo[4,5-d]pyrimidin-3-yl]-2,3-dihydroxycyclopentyl]-2-propenoic acid, sodium salt a) [3aR-(3aα,4α,6α,6aα)]-6-[7-(Ethylamino)-5-(pentylthio)-3H-1,2,3-triazolo-[4,5-d]pyrimidin-3-yl]-tetrahydro-2,2-dimethyl-4H-cyclopenta-1,3-dioxole-4-methanol

MS (FAB): 437 (M+H$^+$, 100%).

b) [3aR-(3aα,4α(E),6α,6aα)]-3-[6-[7-(Ethylamino)-5-(pentylthio)-3H-1,2,3-triazolo[4,5-d]pyrimidin-3-yl]-tetrahydro-2,2-dimethyl-4H-cyclopenta-1,3-dioxol-4-yl]-2-propenoic acid, 1,1-dimethylethyl ester

MS (FAB): 533 (M+H)⁺, 477 (100%).

c) [1R-(1α(E),2β,3β,4aα)]-3-[4-[7-(Ethylamino)-5-(pentylthio-3H-1,2,3-triazolo[4,5-d]pyrimidin-3-yl]-2,3-dihydroxycyclopentyl]-2-propenoic acid, sodium salt MS (FAB): 459 (M+Na+H⁺), 437 (100%).

NMR δH (d₆-DMSO) 8.99 (1H, t), 6.55 (1H, dd), 5.76 (1H, d), 4.98 (1H, q), 4.32 (1H, t), 3.90 (1H, t), 3.81–3.50 (2H, m), 3.16–3.08 (2H, m), 2.74–2.70 (1H, m), 2.46–2.37 (1H, m), 1.98–1.89 (1H, m), 1.71–1.67 (2H, m), 1.37–1.24 (4H, m), 1.19 (3H, t), 0.86 (3H, t,).

Example 6

[1S-(1α,2β,3β,4α)-4-[7-(Butylamino)-5-(pentylthio)-3H-1,2,3-triazolo[4,5-d]pyrimidin-3-yl]-2,3-dihydroxy-cyclopentanepropanoic acid, sodium salt Prepared according to the method of Example 3b) using the product of Example 4.

MS (APCI): 467 (M+H⁺), 295 (100%).

NMR δH (d₆-DMSO) 8.97 (1H, t), 4.93–4.86 (1H, m), 4.32 (1H, t), 3.88 (1H, t), 3.49–3.45 (2H, m), 3.07–3.05 (2H, m), 2.28–2.08 (1H, m), 2.01–1.92 (3H, m), 1.74–1.55 (7H, m), 1.37–1.33 (6H, m), 0.90 (3H, t), 0.86 (3H, t).

Example 7

[1S-(1α,2β,3β,4α)-4-[7-(Ethylamino)-5-(pentylthio)-3H-1,2,3-triazolo[4,5-d]pyrimidin-3-yl]-2,3-dihydroxy-cyclopentanepropanoic acid, sodium salt Prepared according to the method of Example 3b) using the product of Example 5.

MS (FAB): 461 (M+Na+H⁺), 154 (100%).

NMR δH (d₆-DMSO) 8.96 (1H, t), 4.91 (1H, q), 4.33 (1H, t), 3.75 (1H, t), 3.51 (2H, m) 3.08–3.06 (2H, m), 2.30–2.24 (1H, m), 2.06–1.93 (3H, m), 1.75–1.55 (5H, m), 1.37–1.09 (4H, m), 1.15 (3H, t), 0.87 (3H, t).

Example 8

[1R-(1α,2α,3α,5β)]3-[7-(Butylamino)-5-(propylthio)-3H-1,2,3-triazolo-[4,5-d]pyrimidin-3-yl]-5-[2-(1H-tetrazol-5-yl)ethyl]-1,2-cyclopentanediol a) [3aR-(3aα,4α(E),6α,6aα)]-3-[6-[7-(Butylamino)-5-(propylthio)-3H-1,2,3-triazolo[4,5-d]pyrimidin-3-yl]-2,2-dimethyl-tetrahydro-4H-cyclopenta-1,3-dioxole-4-yl]-2-propenonitrile Prepared according to the method of Example 1i) using the product of Example 1h) and (triphenylphosphoranylidene)acetonitrile.

MS (EI): 457 (M⁺), 414 (100%).

b) [3aR-(3aα,4α,6α,6aα)]-3-[6-[7-(Butylamino)-5-(propylthio)-3H-1,2,3-triazolo[4,5-d]pyrimidin-3-yl]-2,2-dimethyl-tetrahydro-4H-cyclopenta-1,3-dioxole-4-yl]-propanenitrile The product of step a) (0.75 g) in ethanol (300 ml) containing 10% palladium on carbon (0.37 g) was stirred under 4 atmospheres of hydrogen for 48 hours. The catalyst was removed by filtration and the filtrate concentrated to afford the subtitle compound (0.34 g).

MS (FAB): 460 (M+H⁺, 100%).

c) [3aS-(3aα,4α,6α,6aα)]-N-Butyl-5-(propylthio)-3-[6-[2-(1H-tetrazol-5-yl)ethyl]-tetrahydro-2,2-dimethyl-4H-cyclopenta-1,3-dioxol-4-yl]-3H-1,2,3-triazolo[4,5-d]-pyrimidin-7-amine The product of step b) (0.40 g) and tributyltin azide (0.70 g) in toluene was heated at reflux for 48 hours then concentrated. Purification by chromatography (SiO₂, dichloromethane:methanol, 95:5 as eluant) gave the subtitle compound (0.19 g).

MS (FAB): 503 (M+H⁺, 100%).

d) [1R-(1α,2α,3β,5β)-3-[7-(Butylamino)-5-(propylthio)-3H-1,2,3-triazol-[4,5-d]pyrimidin-3-yl]-5-[2-(1H-tetrazol-5-yl)ethyl]-1,2-cyclopentanediol Prepared according to the method of Example 1j) using the product of step c).

MS (FAB): 463 (M+H⁺, 100%).

NMR δH (d₆-DMSO) 8.64 (1H, t), 5.11 (1H, m), 4.96 (1H, m), 4.85 (1H, m), 4.38 (1H, m), 3.83 (1H, m), 3.50 (2H, m), 3.07 (2H, m), 2.97 (2H, m), 2.41 (1H, m), 2.00 (2H, m), 1.80 (2H, m), 1.69 (2H, m), 1.61 (2H, m), 1.35 (2H, m), 0.97 (3H, m), 0.91 (3H, t).

Example 9

[1R-(1α,2β,3β,4β)]-N-[3-[4-[7-(Butylamino)-5-(propylthio)-3H-1,2,3-triazolo[4,5-d]pyrimidin-3-yl]-2,3-dihydroxycyclopentyl]propanoyl]-L-aspartic acid a) [1R-(1α,2β,3β,4α)-N-[3-[4-[7-(Butylamino)-5-(propylthio)-3H-1,2,3-triazolo[4,5-d]pyrimidin-3-yl]-2,3-dihydroxycyclopentyl]propanoyl]-L-aspartic acid, bis(1,1-dimethylethyl) ester N,N-Diisopropylethylamine (0.35 ml) was added to a solution of L-aspartic acid di-tertiary butyl ester, hydrochloride (0.28 g), bromo-tris-pyrrolidino-phosphonium hexafluorophosphate (0.44 g) and the product of Example 3 (0.44 g) in DMF (20 ml). The reaction mixture was stirred at room temperature for 1 hr then concentrated. Chromatography (SiO₂, ethyl acetate as eluant) gave the sub-title compound (0.49 g).

MS (APCI) 666 (M+H⁺, 100%).

b) [1R-(1α,2β,3β,4α)]-N-[3-[4-[7-(Butylamino)-5-(propylthio)-3H-1,2,3-triazolo[4,5-d]pyrimidin-3-yl]-2,3-dihydroxycyclopentyl]propanoyl]-L-aspartic acid Prepared according to the method of example 2b) using the product of step a).

NMR δH (d₆-DMSO) 9.03 (1H, brs), 7.79 (1H, d), 4.92 (1H, m), 4.35 (1H, m), 4.19 (1H, t), 3.75 (2H, m), 3.49 (2H, t), 3.08 (2H, m), 2.43 (1H, m), 2.32 (1H, m), 2.18 (3H, m), 1.91 (1H, m), 1.73 (3H, m), 1.58 (2H, m), 1.34 (2H, m), 1.00 (3H, t), 0.98 (3H, t).

Example 10

[1R-(1α(E),2β,3β,4α)-N-[3-[4-[7-(Hexylamino)-5-(propylthio)-3H-1,2,3-triazolo[4,5-d]pyrimidin-3-yl]-2,3-dihydroxycyclopentyl]-2-propenoyl]-L-aspartic acid a) [3aR-(3aα,4α,6α,6aα)-6-[7-(Hexylamino)-5-(propylthio)-3H-1,2,3-triazolo[4,5-d]pyrimidin-3-yl]-tetrahydro-2,2-dimethyl-4H-cyclopenta-1,3-dioxole-4-methanol Sodium borohydride (1.16 g) was added to an ice-cooled solution of the product of step 1e) (5.90 g) in methanol (200 ml). After stirring for 1 hour the solution was concentrated and the residue purified by chromatography (SiO₂, diethyl ether as eluant). The resulting intermediate was taken into acetonitrile (300 ml) and isoamyl nitrite (2.8 ml) added. The reaction mixture was stirred at 60° for 30 minutes then concentrated and the residue taken into 1,4-dioxane (300 ml). Hexylamine (20 ml) was added and the reaction mixture stirred at room temperature for 2 hours. The reaction mixture was concentrated and the residue purified (SiO₂, diethyl ether as eluant) to afford the subtitle compound (4.69 g).

MS (APCI) 465 (M+H⁺, 100%).

b) [1R-(1α(E),2β,3β,4α)]-3-[4-[7-(Hexylamino)-5-(propylthio)-3H-1,2,3-triazolo[4,5-d]pyrimidin-3-yl]-2,3-dihydroxycyclopentyl]-2-propenoic acid Prepared by the method of example 1i) followed by the method of example 1j), using the product of step a).

NMR δH (D₂O) 9.03 (1H, t), 6.96 (1H, dd), 5.89 (1H, d), 5.31 (1H, s), 5.10 (1H, s), 5.00 (1H, m), 4.29 (1H, t), 4.02 (1H, t), 3.49 (2H, m), 3.01 (2H, m), 2.83 (2H, m), 2.49 (1H, m), 2.01 (1H, m), 1.72 (2H, m), 1.65 (2H, m), 1.29 (6H, m), 0.98 (3H, t), 0.86 (3H, t).

c) [1R-(1α(E),2β,3β,4α)]-N-[3-[4-[7-(Hexylamino)-5-(propylthio-3H-1,2,3-triazol[4,5-d]pyrimidin-3-yl]-2,3-dihydroxycyclopentyl]-2-propenoyl]-L-aspartic acid, bis(1,1-dimethylethyl) ester Prepared according to the method of example 9a) using the product of step b).

MS (APCI) 692 (M+H⁺, 100%).

d) [1R-(1α(E),2β,3β,4α)]-N-[3-[4-[7-(Hexylamino)-5-(propylthio)-3H-1,2,3-triazolo[4,5-d]pyrimidin-3-yl]-2,3-dihydroxycyclopentyl]-2-propenoyl]-L-aspartic acid Prepared according to the method of example 2b) using the product of step c).

NMR δH (d₆-DMSO) 7.94 (1H, d), 7.23–7.11 (1H, s), 6.75 (1H, dd), 6.17 (1H, d), 5.19 (1H, s), 5.08 (1H, s), 5.00 (1H, m), 4.31 (2H, m), 3.96 (1H, m), 3.62 (2H, m), 3.07 (2H, m), 2.81 (1H, m), 2.49–2.31 (3H, m), 2.01 (1H, m), 1.67 (2H, m), 1.61 (2H, m), 1.31 (6H, m), 0.96 (3H, t), 0.85 (3H, t).

Example 11

The following compounds were prepared according to the method of example 1.

a) [1R-(1α(E),2β,3β,4α)]-3-[4-[7-(3,3-Dimethylbutylamino)-5-(propylthio)-3H-1,2,3-triazolo[4,5-d]pyrimidin-3-yl]-2,3-dihydroxycyclopentyl]-2-propenoic acid i) [3aR-(3aα,4α,6α,6aα)]-6-[7-(3,3-Dimethylbutylamino)-5-(propylthio)-3H-1,2,3-triazolo[4,5-d]pyrimidin-3-yl]-tetrahydro-2,2-dimethyl-4H-cyclopenta-1,3-dioxole-4-methanol

MS (APCI) 465 (M+H⁺, 100%).

ii) [3aR-(3aα,4α(E),6α,6aα)]-3-[6-[7-(3,3-Dimethylbutylamino)-5-(propylthio)-3H-1,2,3-triazolo[4,5-d]pyrimidin-3-yl]-tetrahydro-2,2-dimethyl-4H-cyclopenta-1,3-dioxol-4-yl ]-2-propenoic acid, 1,1-dimethylethyl ester

MS (APCI) 561 (M+H⁺, 100%).

iii) [1R-(1α(E),2β,3β,4α)]-3-[4-[7-(3,3-Dimethylbutylamino)-5-(propylthio)-3H-1,2,3-triazolo[4,5-d]pyrimidin-3-yl]-2,3-dihydroxycyclopentyl]-2-propenoic acid NMR δH (d₆-DMSO) 8.59 (1H, t), 6.84 (1H, dd), 5.84 (1H, d), 5.03–4.96 (1H, m), 3.98 (1H, m), 3.52 (2H, m), 3.07 (2H, m), 2.81 (1H, m), 2.43 (1H, m), 1.97 (1H, m), 175 (2H, m), 1.55 (2H, m), 0.99 (3H, t), 0.95 (9H, s).

b) [1R-(1α(E),2β,3β,4α)]-3-[4-[7-(2-Methoxy)ethylamino)-5-(propylthio)-3H-1,2,3-triazolo[4,5-d]pyrimidin-3-yl]-2,3-dihydroxycyclopentyl]-2-propenoic acid i) [3aR-(3aα,4α,6α,6aα)]-6-[7-(2-Methoxy)ethylamino)-5-(propylthio)-3H-1,2,3-triazolo[4,5-d]pyrimidin-3-yl]-tetrahydro-2,2-dimethyl-4H-cyclopenta-1,3-dioxole-4-methanol

MS (FAB) 439 (M+H⁺, 100%).

ii) [3aR-(3aα,4α(E),6α,6aα)-3-[6-[7-(2-Methoxy)ethylamino)-5-(propylthio)-3H-1,2,3-triazolo[4,5-d]pyrimidin-3-yl]-tetrahydro-2,2-dimethyl-4H-cyclopenta-1,3-dioxol-4-yl]-2-propenoic acid, 1,1-dimethylethyl ester

MS (FAB) 535 (M+H⁺, 100%).

iii) [1R-(1αa(E),2β,3β,4α)]-3-[4-[7-(2-Methoxy)ethylamino)-5-(propylthio)-3H-1,2,3-triazolo[4,5-d]pyrimidin-3-yl]-2,3-dihydroxycyclopentyl]-2-propenoic acid

MS (FAB) 439 (M+H⁺, 100%).

Example 12

[1R-(1α,2β,3β,4α)-N-[3-[4-[7-(Hexylamino)-5-(propylthio)-3H-1,2,3-triazolo[4,5-d]pyrimidin-3-yl]-2,3-dihydroxycyclopentylpropanoyl]-L-aspartic acid a) [1R-[1α,2β,3β,4α]]-4-[7-(Hexylamino)-5-(propylthio)-3H-1,2,3-triazolo[4,5-d]pyrimidin-3-yl]-2,3-dihydroxycyclopentanepropanoic acid Prepared according to the method of example 3b) using the product of step 10b).

MS (APCI) 467 (M+H⁺, 100%).

b) 1R-(1α,2β,3β,4α)]-N-[3-[4-[7-(Hexylamino)-5-(propylthio)-3H-1,2,3-triazolo[4,5-d]pyrimidin-3-yl]-2,3-dihydroxycyclopentylpropanoyl]-L-aspartic acid, bis(1,1-dimethylethyl) ester Prepared according to the method of example 9a) using the product of step a).

MS (APCI) 694 (M+H⁺, 100%).

c) [1R-(1α,2β,3β,4α)]-N-[3-[4-[7-(Hexylamino)-5-(propylthio)-3H-1,2,3-triazolo[4,5-d]pyrimidin-3-yl]-2,3-dihydroxycyclopentylpropanoyl]-L-aspartic acid Prepared according to the method of example 2b) using the product of step b).

NMR δH (d₆-DMSO) 8.90 (1H, brs), 7.61 (1H, d), 4.97 (1H, m), 4.36 (1H, t), 4.21 (1H, m), 3.47 (2H, m), 3.77 (1H, m), 3.07 (2H, t), 2.51 (2H, m), 2.28 (1H, m), 2.20 (2H, m), 1.93 (1H, m), 1.77 (1H, m), 1.62 (3H, m), 1.59 (3H, m), 1.33 (6H, m), 1.00 (3H, t), 0.88 (3H, t).

Example 13

[1R-(1α(E),2β,3β,4α)-N-[3-[4-[5-[(3,3,3-Trifluoropropyl)thio]-7-[2-(methylthio)ethylamino]-3H-1,2,3-triazolo[4,5-d]pyrimidin-3-yl]-2,3-dihydroxycyclopentyl]-2-propenoyl]-L-aspartic acid, monoammonium salt a) 2-[(3,3,3-Trifluoropropylthio]-4,6(1H,5H)-pyrimidinedione Prepared according to the method of example 1a).

MS (APCI, negative ionization) 239 (M-H⁺), 143 (100%).

b) 2-[(3,3,3-Trifluoropropyl)thio]-6-hydroxy-5-nitro-4(1H)-pyrimidinone

Prepared according to the method of example 1b) using the product of step a).

MS (APCI, negative ionization) 284 (M-H⁺, 100%).

c) 4,6-Dichloro-2-[(3,3,3-trifluoropropyl)thio]-5-nitropyrimidine

Prepared according to the method of example 1c) using the product of step b).

NMR δH (CDCl₃) 3.30 (2H, m), 2.60 (2H, m)

d) [3aS-(3aα,4β,7β,7α)]5-[6-Chloro-2-[(3,3,3-trifluoropropyl)thio]-5-nitro-pyrimidin-4-yl]-tetrahydro-2,2-dimethyl-4,7-methano-1,3-dioxolo[4,5-c]pyridin-6(3aH)-one Prepared according to the method of example 1d) using the product of step c).

NMR δH (CDCl₃) 4.77 (1H, s), 4.73 (1H, d), 4.56 (1H, d), 3.33 (2H, m), 3.05 (1H, s), 2.58 (2H, m), 2.33 (1H, d), 2.20 (1H, t), 1.53 (3H, s), 1.36 (3H, s)

e) [3aS-(3aα,4β,7β,7aα)]5-[5-Amino-6-chloro-2-[3,3,3-trifluoropropyl)thio]pyrimidin-4-yl]-tetrahydro-2,2-dimethyl-4,7-methano-1,3-dioxolo[4,5-c]pyridin-6(3aH)-one Prepared according to the method of example 1e) using the product of step d).

MS (APCI) 439 (M+H⁺, 100%).

f) [3aR-(3aα,4α,6α,6aα)]-6-[[5-Amino-6-chloro-2-[(3,3,3-trifluoropropyl)thio]-4-pyrimidinyl]amino]-tetrahydro-2,2-dimethyl-4H-cyclopenta-1,3-dioxole-4-methanol Prepared according to the method of example 1f) using the product of step e).

MS (APCI) 443 (M+H⁺, 100%).

g) [3aR-(3aα,4α,6α,6aα)]-6-[5-[(3,3,3-Trifluoropropyl)thio]-7-[2-(methylthio)ethylamino]-3H-1,2,3-triazolo[4,5-d]pyrimidin-3-yl]-tetrahydro-2,2-dimethyl-4H-cyclopenta-1,3-dioxole-4-methanol Prepared according to the method of example 1g), followed by the method of example 1h) using the product of step f).

MS (APCI) 509 (M+H⁺, 100%).

h) [3aR-(3aα,4α(E),6α,6aα)]-3-[6-[5-[(3,3,3-Trifluoropropyl)thio]-7-[2-(methylthio)ethylamino]-3H-1,2,3-triazolo[4,5-d]pyrimidin-3-yl]-tetrahydro-2,2-dimethyl-4H-cyclopenta-1,3-dioxol-4-yl]-2-propenoic acid, 1,1-dimethylethyl ester Prepared according to the method of example 1i) using the product of step g).

MS (APCI) 605 (M+H⁺), 549 (100%).

i) [1R-(1α(E),2β,3β,4α)]-3-[4-[5-[(3,3,3-Trifluoropropyl)thio]-7-[2-(methylthio)ethylamino]-3H-1,2,3-triazolo[4,5-d]pyrimidin-3-yl]-2,3-dihydroxycyclopentyl]-2-propenoic acid Prepared according to the method of example 1j) using the product of step h).

MS (APCI) 509 (M+H⁺, 100%).

j) [1R-(1α(E),2β,3β,4α)]-N-[3-[4-[5-[(3,3,3-Trifluoropropyl)thio-7-[2(methylthio)ethylamino]-3H-1,2,3-triazolo[4,5-d]pyrimidin-3-yl]-2,3-dihydroxycyclopentyl]-2-propenoyl]-L-aspartic acid, bis(1,1-dimethylethyl) ester Prepared according to the method of example 9a) using the product of step i).

MS (APCI) 736 (M+H⁺), 624 (100%).

k) [1R-(1α(E),2β,3β,4α)]-N-[3-[4-[5-[(3,3,3-Trifluoropropyl)thio]-7-[2-(methylthio)ethylamino]-3H-1,2,3-triazolo[4,5-d]pyrimidin-3-yl]-2,3-dihydroxycyclopentyl]-2-propenoyl]-L-aspartic acid, monoammonium salt Prepared according to the method of example 2b) using the product of step j).

NMR δH (d₆-DMSO) 7.90 (1H, d), 6.76–6.68 (1H, dd), 6.15 (1H, d), 4.99 (1H, m), 4.30 (2H, m), 3.71 (2H, t), 3.30 (2H, m), 2.74 (5H, m), 2.50 (1H, m), 2.42 (2H, m) 2.11 (3H, s), 1.98 (1H, m).

Example 14

(E)-1-[7-(Butylamino)-5-(propylthio)-3H-1,2,3-triazolo[4,5-d]pyrimidin-3-yl]-1,5,6-trideoxy-β-D-ribo-hept-5-enofuranuronic acid a) 2,6-Bis(propylthio)-4,5-pyrimidinediamine n-Propyl iodide (2.52 ml) was added to a stirred solution of 4,5-diamino-2,6-dimercaptopyrimidine (2.0 g) in 1N potassium hydroxide solution (26.4 ml). On stirring for 24 hours the solid was collected by filtration to give the subtitle compound as a pink solid (2.2 g).

MS (EI): 258 (M⁺, 100%).

b) 5,7-Bis(propylthio)-1H-1,2,3-triazolo[4,5-d]pyrimidine

A solution of sodium nitrite (0.6 g) in water (7 ml) was added to a stirred suspension of the product of step a) (2.0 g) in acetic acid:water (1:1, 90 ml) at 50°. The reaction mixture was stirred at 50° for 1 hour and the solid collected by filtration to give the subtitle compound (1.71 g).

MS (EI): 269 (M⁺), 43 (100%).

c) 5,7-Bis(propylthio)-3-(2,3,5-tri-O-benzoyl-β-D-ribo-furanosyl)-3H-1,2,3-triazolo[4,5-d]pyrimidine Hydrogen bromide gas was bubbled into an ice-cooled solution of 1-O-acetyl-2,3,5-tri-O-benzoyl-β-D-ribofuranose (2.02 g) in dichloromethane (15 ml) for 15 min. The reaction was stirred at 0° for 1 hour then at room temperature for 15 min. The solution was concentrated and the residue azeotroped with dichloromethane (3×50 ml). Sodium hydride (60%, 0.19 g) was added to a stirred suspension of the product of step b) (1.08 g) in acetonitrile (29 ml). After stirring at room temperature for 15 min the bromo sugar described above, in acetonitrile (10 ml), was added and stirring continued for 24 hours. The reaction mixture was partitioned between ethyl acetate and water, the organic layer was dried and concentrated. Chromatography (SiO₂, dichloromethane:diethylether, 39:1, as eluant) gave a mixture of 5,7-bis(propylthio)-3-(2,3,5-tri-O-benzoyl-β-D-ribo-furanosyl)-3H-1,2,3-triazolo[4,5-d]pyrimidine [MS (FAB): 714 (M+H⁺), 105 (100%)] and 5,7-bis(propylthio)-2-(2,3,5-tri-O-benzoyl-β-D-ribo-furanosyl)-2H-1,2,3-triazolo[4,5-d]pyrimidine [MS (FAB): 714 (M+H⁺), 105 (100%)] (1.9 g). Further elution gave 5,7-bis(propylthio)-1-(2,3,5-tri-O-benzoyl-β-D-ribo-furanosyl)-1H-1,2,3-triazolo[4,5-d]pyrimidine as a colourless foam (0.46 g).

MS (FAB): 714 (M+H⁺), 105 (100%).

d) N-Butyl-5-(propylthio)-3-(β-D-ribo-furanosyl)-3H-1,2,3-triazolo[4,5-d]pyriridin-7-amine n-Butylamine (7.37 g) was added to a solution of the mixture of isomers from step c) (9.0 g) in 1,4-dioxane (100 ml), water (30 ml). The solution was heated at 100° for 40 hours then concentrated. The residue was taken into a 0.1M solution of sodium methoxide in methanol (250 ml) and the reaction mixture heated at reflux for 30 mnin. On cooling to room temperature, acetic acid was added to pH7 and the solution concentrated. Chromatography (SiO₂, chloroform:isopropyl alcohol, 85:15, as eluant) gave the subtitle compound as a colourless glass (2.0 g).

MS (Electrospray): 399 (M+H⁺, 100%).

e) N-Butyl-5-(propylthio)-3-[2,3O-(ethoxymethylene)-βD-ribo-furanosyl]-3H-1,2,3-triazolo[4,5-d]pyrimidin-7-amine A solution of the product of step d) (0.40 g) in 1,4-dioxane (5 ml) was treated with trichloroacetic acid (0.44 g) and triethyl orthoformate (0.44 g). The resulting solution was heated at 50° for 90 min. The cooled solution was diluted with dichloromethane (100 ml), washed with saturated sodium bicarbonate solution (50 ml) and water (50 ml), then dried and concentrated. Chromatography (SiO₂, hexane:ethyl acetate, 2:1, as eluant) gave the subtitle compound as a colourless solid (0.32 g).

MS (FAB): 455 (M+H⁺), 267 (100%).

f) (E)-1-[7-(Butylamino)-5-(propylthio)-3H-1,2,3-triazolo[4,5-d]pyrimidin-3-yl]-1,5,6-trideoxy-β-D-ribo-hept-5-enofuranuronic acid, ethyl ester A stirred solution of the product of step e) (3.25 g), pyridine (0.57 g) and trifluoroacetic acid (0.41 g) in DMSO (30 ml) was treated with 1,3-dicyclohexylcarbodiimide (4.42 g) and the mixture stirred at room temperature for 24 hours. Carboethoxymethylenetriphenylphosphorane (3.98 g) was added and the reaction stirred for a further 18 hours. The reaction mixture was cooled to 0°, diluted with ethyl acetate (400 ml) and oxalic acid (3.51 g) added. After 30 min the mixture was filtered and the filtrate washed with saturated sodium bicarbonate solution (200 ml), dried and concentrated. Chromatography (SiO₂, hexane:ethyl acetate, 5:1, as eluant) gave an intermediate which was taken into 80% acetic acid (aq) (25 ml) and heated at 36° for 2 days. The solution was concentrated and the residue purified by chromatography (SiO₂, hexane:ethyl acetate, 2:1, as eluant) to give the subtitle compound as a colourless solid (1.84 g).

MS (FAB): 467 (M+H⁺), 267 (100%).

g) (E)-1-[7-(Butylamino)-5-(propylthio)-3H-1,2,3-triazolo[4,5-d]pyrimidin-3-yl]-1,5,6-trideoxy-β-D-ribo-hept-5-enofuranuronic acid Prepared according to the method of Example 3c) using the product of step f).

NMR δH (d₆-DMSO) 9.10 (1H, t), 6.82 (1H, dd), 6.15 (1H, d), 5.89 (1H, d), 476 (1H, t), 4.60 (1H, t), 4.39 (1H, t), 3.50 (2H, m), 3.08 (2H, m), 1.69 (2H, m), 1.61 (2H, m), 134 (2H, m), 0.98 (3H, t), 0.91 (3H, t).

MS (FAB): 439 (M+H⁺), 267 (100%).

Example 15

(E)-N-[1-[7-(Butylamino)-5-(propylthio)-3H-1,2,3-triazolo[4,5-d]pyrimidin-3-yl]-1,5,6-trideoxy-β-D-ribo-hept-5-enofuranuronoyl]-L-aspartic acid a) (E)-N-[1-[7-(Butylamino)-5-(propylthio)-3H-1,2,3-triazolo[4,5-d]pyrimidin-3-yl]-1,5,6-trideoxy-β-D-ribo-hept-5-enofuranuronoyl]-L-aspartic acid, bis(1,1-dimnethylethyl) ester Prepared according to the method of Example 2a) using the product of Example 14.

MS (Electrospray): 666 (M+H⁺, 100%).

b) (E)-N-[1-[7-(Butylamino)-5-(propylthio)-3H-1,2,3-triazolo[4,5-d]pyrimdin-3-yl]-1,5,6-trideoxy-β-D-ribo-hept-5-enofuranuronoyl]-L-aspartic acid Prepared according to the method of Example 2b) using the product of step a).

NMR δH (d₆-DMSO): 12.57 (2H, brs), 9.09 (1H, t), 8.42 (1H, d), 6.70 (1H, dd), 6.13 (2H, m), 5.78 (1H, d), 5.60 (1H, d), 4.71 (1H, m), 4,56 (2H, m), 4.40 (1H, q), 3.50 (2H, q), 3.07 (2H, m), 2.63 (2H, m), 1.68 (2H, m), 1.60 (2H, m), 1.35 (2H, m), 0.98 (3H, t), 0.91 (3H, t).

Example 16

The following compound was prepared according to the method of Examples 14 and 15:

(E)-N-[1-[7-Amino-5-(propylthio)-3H-1,2,3-triazolo[4,5-d]pyrimidin-3-yl]-1,5,6-trideoxy-β-D-ribo-hept-5-enofuranuronoyl]-L-aspartic acid, monoammonium salt a) 5-(Propylthio)-3-(β-D-ribo-furanosyl)-3H-1,2,3-triazolo[4,5-d]pyrimidin-7-amine A solution of the mixture of isomers from Example 14c) (12.0 g) in methanol (1 L) was cooled to 0° and saturated with ammonia gas. The solution was stirred at room temperature for 72 hours then concentrated. Chromatography (SiO₂, dichloromethane:methanol, 14:1, as eluant) gave the subtitle compound as a colourless solid (4.94 g).

MS (Electrospray): 343 (M+H⁺, 100%).

b) 5-(Propylthio)-3-[2,3O-(ethoxymethylene)-β-D-ribo-furanosyl]-3H-1,2,3-triazolo[4,5-d]pyrirdin-7-amine MS (Electrospray): 399(M+H⁺, 100%).

c) (E)-1-[7-Amino-5-(propylthio)-3H-1,2,3-triazolo[4,5-d]pyrimidin-3-yl]-1,5,6-trideoxy-β-D-ribo-hept-5-enofuranuronic acid, ethyl ester MS (Electrospray): 411 (M+H⁺, 100%).

d) (E)-1-[7-Amino-5-(propylthio)-3H-1,2,3-triazolo[4,5-d]pyrimidin-3-yl]-1,5,6-trideoxy-β-D-ribo-hept-5-enofuranuronic acid ester MS (Electrospray): 383 (M+H⁺, 100%).

e) (E)-N-[1-[7-Amino-5-(propylthio)-3H-1,2,3-triazolo[4,5-d]pyrimidin-3-yl]-1,5,6-trideoxy-β-D-ribo-hept-5-enofuranuronoyl]-L-aspartic acid, bis(1,1-dimethylethyl) ester MS (Electrospray): 610 (M+H⁺, 100%).

f) (E)-N-[1-[7-Amino-5-(propylthio)-3H-1,2,3-triazolo[4,5-d]pyrimidin-3-yl]-1,5,6-trideoxy-β-D-ribo-hept-5-enofuranuronoyl]-L-aspartic acid, monoammonium salt NMR δH (d₆-DMSO): 8.53 (1H, brs), 8.18 (1H, brs), 6.66 (1H, dd), 6.62 (1H, d), 6,15 (1H, d), 4.78 (1H, t), 4.54 (1H, t), 4.39 (1H, t), 4.25 (1H, m), 3.05 (2H, m), 2.53–2.25 (2H, m), 1.68 (2H, m), 0.97 (3H, t).

Example 17

(E)-N-[1-[7-(Butylamino)-5-(propylthio)-3H-1,2,3-triazolo[4,5-d]pyrimidin-3-yl]-1,5,6-trideoxy-β-D-ribo-heptofuranuronoyl]-L-aspartic acid, monoammonium salt a) (E)-1-[7-(Butylamino)-5-(propylthio)-3H-1,2,3-triazolo[4,5-d]pyrimidin-3-yl]-1,5,6-trideoxy-β-D-ribo-heptofuranuronic acid, ethyl ester Prepared according to the method of Example 3b) using the product of step 14f).

MS (Electrospray): 469 (M+H⁺, 100%).

b) (E)-1-[7-(Butylamino)-5-(propylthio)-3H-1,2,3-triazolo[4,5-d]pyrimidin-3-yl]-1,5,6-trideoxy-β-D-ribo-heptofuranuronic acid Prepared according to the method of Example 3c) using the product of step a).

MS (Electrospray, negative ionization): 439 (M-H⁺, 100%).

c) (E)-N-[1-[7-(Butylamino)-5-(propylthio)-3H-1,2,3-triazolo[4,5-d]pyrimidin-3-yl]-1,5,6-trideoxy-β-D-ribo-heptofuranuronoyl-L-aspartic acid, bis (1,1-dimethylethyl) ester Prepared according to the method of Example 2a) using the product of step b).

MS (Electrospray): 668 (M+H⁺, 100%).

d) (E)-N-[1-[7-(Butylamino)-5-(propylthio)-3H-1,2,3-triazolo[4,5-d]pyrimidin-3-yl]-1,5,6-trideoxy-β-D-ribo-heptofuranuronoyl]-L-aspartic acid, monoammonium salt Prepared according to the method of Example 2b) using the product of step c).

NMR δH (d₆-DMSO): 9.07 (1H, t), 7.69 (1H, d), 6.04 (1H, d), 5.50 (2H, brs), 4.76 (1H, t), 4.18 (2H, m), 3.91 (1H, m), 3.49 (2H, q), 3.08 (2H, t), 2.46–2.23 (2H, m), 2.18 (2H, t), 1.93 (1H, m), 1.70 (3H, m), 1.60 (2H, m), 1.34 (2H, m), 0.99 (3H, t), 0.91 (3H, t).

Example 18

(E)-N-[1,5,6-Trideoxy-1-[7-(hexylamino)-5-(propylthio)-3H-1,2,3-triazolo-[4,5-d]pyrimidin-3-yl]-β-D-ribo-hept-5-enofuranuronoyl]-L-aspartic acid, monoammonium salt a) 3-(5-O-Benzoyl-β-D-ribo-furanosyl)-N-hexyl-5-(propylthio)-3H-1,2,3-triazolo[4,5-d]pyrimidin-7-amine Prepared according to the method of Example 14d) using n-hexylamine.

MS (FAB): 531 (M+H⁺), 295 (100%).

b) 3-[5O-Benzoyl-2,3-O-(1-methylethylidene)-β-D-ribo-furanosyl]-N-hexyl-5-(propylthio)-3H-1,2,3-triazolo[4,5-d]pyrimidin-7-amine The product of step a) (4.93 g) in acetone (120 ml), containing 2,2-dimethoxypropane (11.4 ml) was treated with p-toluenesulfonic acid (4.4 g). The resulting solution was stirred at room temperature for 2 hours, basified with triethylamine (3.25 ml) and concentrated. Chromatography (SiO₂, cyclohexane:ethanol, 95:5 as eluant) gave the subtitle compound (5.03 g).

MS (Electrospray): 571 (M+H⁺, 100%).

c) N-Hexyl-3-[2,3-O-(1-methylethylidene)-β-D-ribofuranosyl]-5-(propylthio)-3H-1,2,3-triazolo[4,5-d]pyrimidin-7-amine A solution of the product of step b) (5.02 g) in a 0.1M solution of sodium methoxide in is methanol (88 ml) was heated at reflux for 30 min. Acetic acid (1 ml) was added and the reaction concentrated. Chromatography (SiO$_2$, dichloromethane:acetonitrile, 95:5 as eluant) gave the subtitle compound (3.63 g).

MS (Electrospray): 467 (M+H$^+$, 100%).

d) (E)-1,5,6-Trideoxy-1-[7-(hexylamino)-5-(propylthio)-3H-1,2,3-triazolo-[4,5-d]pyrimidin-3-yl]-2,3-O-(1-methylethylidene)-β-D-ribo-hept-5-enofuranuronic acid, 1,1-dimethylethyl ester Prepared according to the method of Example 1i) using the product of step c).

MS (FAB): 563 (M+H$^+$, 100%).

e) (E)-1,5,6-Trideoxy-1-[7-(hexylamino)-5-(propylthio)-3H 1,2,3-triazolo-[4,5-d]pyrimidin-3-yl]-β-D-ribo-hept-5-enofuranuronic acid Prepared according to the method of Example 1j) using the product of step d).

MS (FAB): 467 (M+H$^+$), 295 (100%).

f)(E)-N-[1,5,6-Trideoxy-1-[7-(hexylamino-5-(propylthio)-3H-1,2,3-triazolo-[4,5-d]pyrimidin-3-yl]-βD-ribo-hept-5-enofuranuronoyl]-L-aspartic acid, bis(1,1-dimethylethyl) ester Prepared according to the method of Example 9a) using the product of step e).

MS (FAB): 694 (M+H$^+$), 295 (100%).

g) (E)-N-[1,5,6-Trideoxy-1-[7-(hexylamino-5-(propylthio)-3H-1,2,3-triazol-[4,5-d]pyimidin-3-yl]-β-D-ribo-hept-5-enofuranuronoyl]-L-aspartic acid, monoarmonium salt Prepared according to the method of Example 2b) using the product of step f).

MS (FAB): 582 (M+H$^+$), 295 (100%).

NMR δH (d$_6$-DMSO) 8.74 (1H, t), 8.00 (1H, m), 6.66 (1H, dd), 6.23 (1H, d), 6.15 (1H, m), 4.76 (1H, m), 4.55 (1H, t), 4.40 (1H, t), 4.27 (1H, t), 3.50 (2H, m), 3.07 (2H, m), 2.51 (2H, m), 1.68 (4H, m), 1.30 (6H, m), 0.98 (3H, m), 0.87 (3H, m).

Example 19

(E)-1-[7-(N-Butyl-N-methyl-amino)-5-(propylthio)-3H-1,2,3-triazolo[4,5-d]-pyrimidin-3-yl]-1,5,6-trideoxy-β-D-ribo-hept-5-enofuranuronic acid a) N-Butyl-N-methyl-5-(propylthio)-3-(β-D-ribo-furanosyl)-3H-1,2,3-triazolo-[4,5-d]pyrimidin-7-amine Prepared according to the method of Example 14d), using N-methylbutylamine.

MS (FAB): 413 (M+H$^+$), 281 (100%).

b) N-Butyl-N-methyl-5-(propylthio)-3-[2,3-O-(1-methylethylidene)-β-D-ribo-furanosyl]-3H-1,2,3-triazolo[4,5-d]pyrimidin-7-amine Prepared according to the method of Example 18b) using the product of step a).

MS (FAB): 453 (M+H$^+$), 281 (100%).

c) (E)-1-[7-(N-Butyl-N-methyl-amino)-5-(propylthio)-3H-1,2,3-triazolo[4,5-d]-pyrimidin-3-yl]-1,5,6-trideoxy-2,3-O-(1-methylethylidene)-β-D-ribo-hept-5-enofuranuronic acid, 1,1-dimethylethyl ester Prepared according to the method of Example 1i) using the product of step b).

MS (FAB): 549 (M+H$^+$, 100%).

d) (E)-1-[7-(N-Butyl-N-methyl-amino)-5-(propylthio)-3H-1,2,3-triazolo[4,5-d]-pyrimidin-3-yl]-1,5,6-trideoxy-β-D-ribo-hept-5-enofuranuronic acid Prepared according to the method of Example 1j) using the product of step c).

MS (FAB): 453 (M+H$^+$, 100%).

NMR δH (d$_6$-DMSO) 6.51 (1H, dd), 6.12 (1H, d), 5.83 (1H, d), 4.71 (1H, t), 4.51 (1H, t), 4.31 (1H, m), 3.76 (2H, m), 3.71 (3h, s), 3.08 (2H, m), 1.69 (4H, m), 1.61 (2H, m), 1.34 (2H, m), 0.94 (6H, m).

Example 20

(E)-N-[1-[7-(Butylamino)-5-(methylthio)-3H-1,2,3-triazolo[4,5-d]pyrimidin-3-yl]-1,5,6-trideoxy-β-D-ribo-hept-5-enofuranuronoyl]-L-aspartic acid a) 3-(2,3,5-Tri-O-benzoyl-β-D-ribo-furanosyl)-5,7-bis (methylthio)-3H-1,2,3-triazolo[4,5-d]pyrimidine, and 2-(2,3,5-Tri-O-benzoyl-β-D-ribo-furanosyl)-5,7-bis(methylthio)-2H-1,2,3-triazolo[4,5-d]pyrmidine Prepared according to the method of Example 14c) using 5,7-bis(methylthio)-1H-triazolo[4,5-d]pyrimidine (prepared by the method described by J. A. Montgomery, A. T. Shortnacy, G. Arnett, W. H. Shannon, *J. Med. Chem.*, 1977, 20, 401.). Chromatography (SiO$_2$, dichloromethane:ethyl acetate, 99:1 as eluant) gave the subtitle compounds (13.3 g).

MS (Electrospray): 658 (M+H$^+$, 100%).

b) N-Butyl-3-[2,3-O-(1-methylethylidene)-β-D-ribo-furanosyl]-5-(methylthio)-3H-1,2,3-triazolo[4,5-d]pyrimidin-7-amine n-Butylamine (13.5 ml) was added to a solution of the mixture of isomers from step a) (22.5 g) in dioxane (175 ml)/water (25 ml). The solution was stirred at room temperature for 24 hours then concentrated. The residue was taken into a 0.1M solution of sodium methoxide in methanol (500 ml) and heated at reflux for 30 mimn. On cooling to room temperature the solution was concentrated and the residue taken into DMF (80 ml). p-Toluenesulfonic acid (5.91 g) and 2,2-dimethoxypropane (50 ml) were added and the reaction mixture stirred at room temperature for 24 hours. The solution was concentrated and the residue partitioned between ethyl acetate (500 ml) and saturated sodium bicarbonate solution (500 ml), the organic phase was dried and concentrated. Chromatography (SiO$_2$, hexane:ethyl acetate, 7:3 as eluant) gave the subtitle compound as a colourless solid (3.67 g).

MS (Electrospray): 411 (M+H$^+$, 100%).

c)(E)-1-[7-(Butylamino)-5-(methylthio)-3H-1,2,3-triazolo[4,5-d]pyrimidin-3-yl]-1,5,6-trideoxy-2,3-O-(1-methylethylidene)-β-D-ribo-hept-5-enofuranuronic acid, ethyl ester Prepared according to the method of Example 1i) using the product of step b) and (carbethoxymethylene) triphenylphosphorane.

MS (FAB): 479 (M+H$^+$, 100%).

d)(E)-1-[7-(Butylamino)-5-(methylthio)-3H-1,2,3-triazolo[4,5-d]pyrimidin-3-yl]-1,5,6-trideoxy-β-D-ribo-hept-5-enofuranuronic acid, ethyl ester The product of step c) (1.4 g) was taken into a 2M solution of HCl in methanol (75 ml) and the reaction mixture stirred at room temperature for 15 min then concentrated. The residue was taken into ethyl acetate (300 ml), washed with saturated sodium bicarbonate solution (3×100 ml), dried and concentrated. Chromatography (SiO$_2$, dichloromethane:methanol, 97:3 as eluant) gave the subtitle compound as a colourless solid (1.10 g).

MS (FAB): 439 (M+H$^+$), 239 (100%).

e) (E)-1-[7-(Butylamino)-5-(methylthio)-3H-1,2,3-triazolo[4,5-d]pyrimidin-3-yl]-1,5,6-trideoxy-β-D-ribo-hept-5-enofuranuronic acid Prepared according to the method of Example 3c) using the product of step d).

MS (FAB): 411 (M+H$^+$), 154 (100%).

f) (E)-N-[1-[7-(Butylamino)-5-(methylthio)-3H-1,2,3-triazolo[4,5-d]pyrimidin-3-yl]-1,5,6-trideoxy-β-D-ribo-hept-5-enofuranuronoyl]-L-aspartic acid, bis(1,1-dimethylethyl) ester Prepared according to the method of Example 2a) using the product of step e).

MS (FAB): 638 (M+H$^+$), 239 (100%).

g) (E)-N-[1-[7-Butylamino)-5-(methylthio)-3H-1,2,3-triazolo[4,5-d]pyrimidin-3-yl]-1,5,6-trideoxy-β-D-ribo-hept-5-enofuranuronoyl-L-aspartic acid Prepared according to the method of Example 2b) using the product of step f).

MS (FAB): 526 (M+H$^+$), 239 (100%).

Example 21

(E)-1-[5-Butyl-7-(butylamino)-3H-1,2,3-triazolo[4,5-d]pyrimidin-3-yl]-1,5,6-trideoxy-β-D-ribo-hept-5-enofuranuronic acid a) 5-Butyl-3,4-dihydro-3-[2,3-O-(1-methylethylidene)-β-D-ribo-furanosyl]-7H-1,2,3-triazolo[4,5-d]pyrimidin-7-one Sodium (4.6 g) was dissolved in ethanol (200 ml) then 5-amino-1-[2,3-O-(1-methylethylidene)-β-D-ribo-furanurosyl]-1H-1,2,3-triazole-4-carboxamide (prepared as described by G. Biagi et al, Farmaco, 1992, 47, 525) (6.0 g) added and the mixture heated to reflux. Methyl valerate (10.5 ml) was added and reflux maintained for 17 hours. The mixture was neutralised using Dowex 50×8-200 (H$^+$ form), filtered and the filtrate concentrated. The residue was taken into ethanol, acetic acid added and the solution concentrated. Chromatography (SiO$_2$, hexane:ethyl acetate, 7:3 as eluant) gave the subtitle compound as a colourless oil (3.08 g).

MS (FAB): 366 (M+H$^+$).

b) 5-Butyl-3,4-dihydro-3-[5-O-acetyl-2,3-O-(1-methylethylidene-β-D)-ribo-furanosyl]-7H-1,2,3-triazolo[4,5-d]pyrimidin-7-one Triethylamine (0.42 g) and acetyl chloride (0.3 g) were added sequentially to an ice-cooled solution of the product from step a) (1.41 g) in dichloromethane (50 ml). The mixture was stirred at 5° for 30 min then washed with brine, dried and concentrated. Chromatography (SiO$_2$, dichloromethane:methanol, 95:5 as eluant) gave the subtitle compound (1.2 g).

MS (EI): 408 (M+H$^+$).

c) 5-Butyl-7-chloro-3-[5-O-acetyl-2,3-O-(1-methylethylidene)-β-D-ribo-furanosyl]-3H-1,2,3-triazolo[4,5-d]pyrimidine The product from step b) (1.19 g) and DMF (299 mg) in chloroform (30 ml) was heated to reflux, thionyl chloride (3.47 g) was added and reflux maintained for 45 min. After cooling in an ice bath, the mixture was added slowly to a stirred, saturated solution of sodium bicarbonate. The mixture was extracted with dichloromethane (3×200 ml) and the combined organics dried, filtered and concentrated. Chromatography (SiO$_2$, hexane:ethyl acetate, 5:1 as eluant) gave the subtitle compound (1.14 g).

MS (EI): 427, 425 (M+H$^+$).

d) N,5-Di(butyl)-3-[2,3-O-(1-methylethylidene)-β-D-ribo-furanosyl]-3H-1,2,3-triazolo[4,5-d]pyrimidin-7-amine Prepared according to the method of Example 1h) using the product of step c).

MS (EI): 420 (M$^+$).

e) (E)-1-[5-Butyl-7-(butylamino)-3H-1,2,3-triazolo[4,5-d]pyrimidin-3-yl]-1,5,6-trideoxy-2,3-O-(1-methylethylidene)-β-D-ribo-hept-5-enofuranuronic acid, 1,1-dimethylethyl ester Prepared according to the method of Example 1i) using the product of step d).

MS (FAB): 517 (M+H$^+$, 100%).

f) (E)-1-[5-Butyl-7-(butylamino)-3H-1,2,3-triazolo[4,5-d]pyrimidin-3-yl]-1,5,6-trideoxy-β-D-ribo-hept-5-enofuranuronic acid Prepared according to the method of Example 1j) using the product of step e).

NMR δH (d$_6$-DMSO): 8.87 (1H, t), 6.71 (1H, dd), 6.20 (1H, m), 5.89 (1H, d), 4.75 (1H, m), 4.56 (1H, t), 4.37 (1H, t), 3.54 (2H, q), 2.73 (2H, t), 1.74 (2H, m), 1.62 (2H, m), 1.35 (4H, m), 0.91 (6H, t).

Example 22

(E)-1-[7-Butyl-5-(propylthio)-3H-1,2,3-triazolo[4,5-d]pyrimidin-3-yl]-1,5,6-trideoxy-β-D-ribo-hept-5-enofuranuronic acid a) 5-Amino-1-[5-O-[(1,1-dimethylethyl)dimethylsilyl]-2,3-O-(1-methylethylidene)-β-D-ribofuranurosyl]-1H-1,2,3-triazole-4-carboxamide A solution of 5-amino-1-[2,3-O-(1-methylethylidene)-β-D-ribofuranurosyl]-1H-1,2,3-triazole-4-carboxamide (prepared as described by G. Biagi et al, Farmaco, 1992, 47, 525) (10.0 g), imidazole (2.20 g) and tert-butyldimethylsilyl chloride (4.98 g) in DMF (200 ml) was stirred at room temperature for 16 hours. The solution was concentrated and the residue purified (SiO$_2$, dichloromethane:ethyl acetate, 1:1 as eluant) to give the subtitle compound (12.0 g).

MS (EI): 398 (M–CH$_3$$^+$), 73 (100%).

b) 3,6-Dihydro-3-[5-O-[(1,1-dimethylethyl)dimethysilyl]-2,3-O-(1-methylethylidene)-β-D-ribo-furanosyl]-5-mercapto-7H-1,2,3-triazolo[4,5-d]pyrimidin-7-one The product of step a) (26.0 g) in DMF (100 ml) was added, over 1 hour, to a stirred suspension of sodium hydride (60%, 2.52 g) in DMF (200 ml). 1,1-Thiocarbonyldiimidazole (11.2 g) was added and the reaction mixture heated at reflux for 1 hour then concentrated. The residue was taken into water (1 L), acidified with glacial acetic acid and the subtitle compound isolated by filtration (14.1 g).

MS (FAB): 456 (M+H$^+$), 69 (100%).

c) 3-[5-O-[(1,1-Dimethylethyl)diethylsilyl]-2,3-O-(1-methylethylidene)-β-D-ribo-furanosyl]-3,4-dihydro-5-(propylthio)-7H-1,2,3-triazolo[4,5-d]pyrimidin-7-one The product of step b) (19.3 g) was added to a stirred suspension of sodium hydride (60%, 1.41 g) in DMF (200 ml). After 15 min iodopropane (3.55 ml) was added and the mixture stirred for 1 hour then concentrated. The residue was partitioned between water (1 L) and dichloromethane (1 L). The organic layer was dried and concentrated to give the subtitle compound (18 g).

MS (FAB): 498 (M+H$^+$), 73 (100%).

d) 3-[2,3-O-(1-Methylethylidene)-β-D-ribo-furanosyl]-3,4-dihydro-5-(propylthio)-7H-1,2,3-triazolo[4,5-d]pyrimidin-7-one Tetrabutylammonium fluoride (1M in THF, 40.6 ml) was added to a stirred solution of the product of step c) (20.2 g) in THF (300 ml) and the reaction mixture stirred at room temperature for 12 hours. The solution was concentrated and the residue partitioned between water (1 L) and ethyl acetate (1 L). The organic phase was dried and concentrated to give the subtitle compound (14.1 g).

MS (Electrospray): 382 (M–H$^+$, 100%).

e) 3-[5-O-Acetyl-2,3-O-(1-methylethylidene)-β-D-ribo-furanosyl]-3,4-dihydro-5-(propylthio)-7H-1,2,3-triazolo[4,5-d]pyrimidin-7-one Prepared according to the method of Example 21b) using the product of step d).

MS (Electrospray): 443 (M+H⁺, 100%).

f) 3-[5-O-Acetyl-2,3-O-(1-methylethylidene)-βD-ribo-furanosyl]-7-chloro-5-(propylthio)-3H-1,2,3-triazolo[4,5-d]pyrimidine Prepared according to the method of Example 21c) using the product of step e).

MS (FAB): 444, 446 (M+H⁺).

g) 3-[5-O-Acetyl-2,3-O-(1-methylethylidene)-β-D-ribo-furanosyl]-7-butyl-5-(propylthio)-3H-1,2,3-triazolo[4,5-d]pyrimidine Bis(triphenylphosphine)palladium(II) chloride (40 mg) and tetrabutyltin (0.81 ml) were added to a solution of the product from step f) (500 mg) in 1-methyl-2-pyrrolidinone (5 ml) and the mixture stirred at 100° for 2 hours, then at room temperature for 72 hours. The mixture was partitioned between water (100 ml) and ethyl acetate (200 ml), the organic layer washed with brine (50 ml), dried and concentrated. Chromatography (SiO₂, hexane:ethyl acetate 85:15 as eluant) gave the subtitle compound (230 mg).

MS (FAB): 466 (M+H⁺).

h) 7-Butyl-3-[2,3-O-(1-methylethylidene)-β-D-ribo-furanosyl]-5-(propylthio)-3H-1,2,3-triazolo[4,5-d]pyrimidine Prepared according to the method of Example 16a) using the product of step g).

MS (FAB): 424 (M+H⁺).

i) (E)-1-[7-Butyl-5-(propylthio)-3H-1,2,3-triazolo[4,5-d]pyrimidin-3-yl]-1,5,6-trideoxy-β-D-ribo-hept-5-enofuranuronic acid, 1,1-dimethylethyl ester Prepared according to the method of Example 1i) using the product of step h).

MS (FAB): 520 (M+H⁺).

j) (E)-1-[7-Butyl-5-(propylthio)-3H-1,2,3-triazolo[4,5-d]pyrimidin-3-yl]-1,5,6-trideoxy-β-D-ribo-hept-5-enofuranuronic acid Prepared according to the method of Example 2b) using the product of step i).

NMR δH (CDCl₃): 7.00 (1H, d), 6.52 (1H, s), 6.01 (1H, d), 5.30 (2H, brs), 4.94 (1H, s), 4.56 (1H, t), 4.76–4.81 (2H, d), 3.12 (4H, brs), 1.80 (2H, q), 1.70 (2H, q), 1.37 (2H, q), 0.99 (3H, t), 0.89 (3H, t).

Example 23

(E)-N-[1-[5,7-Di(butylamino)-3H-1,2,3-triazolo[4,5-d]pyrimidin-3-yl]-1,5,6-trideoxy-β-D-ribo-heptofuranuronoyl]-L-aspartic acid, monoamimonium salt a) (E)-N-[1-[7-Butylamino-5-(methylsulfonyl)-3H-1,2,3-triazolo[4,5-d]-pyrimidin-3-yl]-1,5,6-trideoxy-β-D-ribo-heptofuranuronoyl]-L-aspartic acid, bis(1,1-dimethylethyl) ester 3-Chloroperoxybenzoic acid (50%, 0.12 g) in ethanol (1 ml) was added, over 1 hour, to a stirred solution of the product of Example 17c) (0.1 g) in ethanol (2 ml). After stirring at room temperature for 16 hours the solution was diluted with dichloromethane (50 ml) then washed with aqueous sodium metabisulfite solution (30 ml) and aqueous sodium carbonate solution (2×20 ml). The organic layer was dried and concentrated to give the subtitle compound (90 mg).

MS (FAB): 700 (M+H⁺), 299 (100%).

b) (E)-N-[1-[5,7-Di(butylamino)-3H-1,2,3-triazolo[4,5-d]pyrimidin-3-yl]-1,5,6-trideoxy-β-D-ribo-heptofuranuronoyl]-L-aspartic acid, bis(1,1-dimethylethyl) ester Prepared according to the method of Example 1h) using the product of step a).

MS (FAB): 665 (M+H⁺, 100%).

c) (E)-N-[1-[5,7-Di(butylamino)-3H-1,2,3-triazolo[4,5-d]pyrimidin-3-yl]-1,5,6-trideoxy-β-D-ribo-heptofuranuronoyl]-L-aspartic acid, monoammonium salt Prepared according to the method of Example 2b) using the product of step b).

MS (Electrospray): 553 (M+H⁺, 100%).

Example 24

(Z)-1-[7-(Butylamino)-5-(propylthio)-3H-1,2,3-triazolo[4,5-d]pyrimidin-3-yl]-1,5,6-trideoxy-β-D-ribo-hept-5-enofuranuronic acid a) N-Butyl-5-(propylthio)-3-[2,3-O-(1-methylethylidene)-β-D-ribo-furanosyl]-3H-1,2,3-triazolo[4,5-d]pyrimidin-7-amine Prepared according to the method of Example 18b) using the product of Example 14e).

MS (FAB): 439 (M+H⁺), 267 (100%).

b) (Z)-1-[7-(Butylamino)-5-(propylthio)-3H-1,2,3-triazolo[4,5-d]pyrimidin-3-yl]-1,5,6-trideoxy-2,3-O-(1-methylethylidene)-β-D-ribo-hept-5-enofuranuronic acid, 1,1-dimethylethyl ester Prepared according to the method of Example 1i) using the product of step a), the subtitle compound was isolated as a minor product.

MS (FAB): 535 (M+H⁺, 100%).

c) (Z)-1-[7-(Butylamino)-5-(propylthio)-3H-1,2,3-triazolo[4,5-d]pyrimidin-3-yl]-1,5,6-trideoxy-β-D-ribo-hept-5enofuranuronic acid Prepared according to the method of Example 1j) using the product of step b).

MS (FAB): 439 (M+H⁺), 267 (100%).

NMR δH (d₆-DMSO) 8.76 (1H, t), 6.22 (1H, m), 6.14 (1H, m), 5.85 (1H, d), 5.48 (1H, m), 4.84 (1H, t), 4.25 (1H, m), 3.50 (2H, m), 3.09 (2H, m), 1.71 (2H, m), 1.63 (2H, m), 1.35 (2H, m), 0.99 (3H, t), 0.91 (3H, t).

Example 25

N-Butyl-5-(propylthio)-3-[5,6-dideoxy-6-(1H-tetrazol-5-yl)-β-D-ribo-hexofuranosyl]-3H-1,2,3-triazolo[4,5-d]pyrimidine-7-amine a) (E)-1-[7-(Butylamino)-5-(propylthio)-3H-1,2,3-triazolo[4,5-d]pyrimidin-3-yl]-1,5,6-trideoxy-2,3-O-(1-methylethylidene)-β-D-ribo-hept-5-enofuranurononitrile Prepared according to the method of Example 1i) using the product of step 24a) and (triphenylphosphoranylidene)acetonitrile.

MS (FAB): 460 (M+H⁺, 100%).

b) (E)-1-[7-(Butylamino)-5-(propylthio)-3H-1,2,3-triazolo[4,5-d]pyrimidin-3-yl]-1,5,6-trideoxy-2,3-O-(1-methylethylidene)-β-D-ribo-heptofuranurononitrile Prepared according to the method of Example 8b) using the product of step a).

MS (APCI): 462 (M+H⁺, 100%).

c) N-Butyl-5-(propylthio)-3-[5,6-dideoxy-2,3-O-(1-methylethylidene)-6-(1H-tetrazol-5-yl)-β-D-ribo-hexofuranosyl]-3H-1,2,3-triazolo[4,5-d]pyrimidine-7-amine Azidotrimethylsilane (0.30 g) and dibutyltin oxide (32 mg) were added to a solution of the product of step b) (0.60 g) in toluene (6 ml) and the resulting solution heated under reflux for 72 hours. On cooling to room temperature the solvent was removed and the residue purified by chromatography (SiO₂, ethyl acetate:isohexane:acetic acid, 100:100:1 as eluant) to give the subtitle compound (0.26 g).

MS (FAB): 505 (M+H⁺), 267 (100%).

d) N-Butyl-5-(propylthio)-3-[5,6-dideoxy-6-(1H-tetrazol-5-yl)-β-D-ribo-hexofuranosyl]-3H-1,2,3-triazolo[4,5-d]pyrimidine-7-amine Prepared according to the method of Example 1j) using the product of step c). The crude product was triturated with ethyl acetate to give the title compound (0.13 g).

MS (FAB): 465 (M+H$^+$), 267 (100%).

NMRδH (d$_6$-DMSO) 9.08 (1H, t), 6.08 (1H, d), 5.65 (1H, d), 5.35 (1H, m), 4.76(1H, t), 4.30 (1H, t), 3.98 (1H, m), 3.50 (2H, m), 3.06 (2H, m), 2.92 (2H, m), 2.05 (2H, m), 1.63 (4H, m), 1.34 (2H, m), 0.97 (3H, t), 0.91 (3H, t).

Example 26

1,5,6-Trideoxy-1-[5,7-bis(propylthio)-3H-1,2,3-triazolo[4,5-d]pyrimidin-3-yl]-β-D-ribo-heptofuranuronic acid, sodium salt a) (E)-1,2,3-Tri-O-acetyl-5,6-dideoxy-β-D-ribo-hept-5-enofuranuronic acid, ethyl ester (E)-Methyl 5,6dideoxy-2,3-O-(1-methylethylidene)-β-D-ribo-hept-5-enofuranosiduronic acid, ethyl ester (prepared as described by A. J. Cooper, R. G. Salomon, *Tetrahedron Lett.*, 1990, 31, 3813) (8.0 g) was heated at 80° in a mixture of acetic acid (256 ml) and water (64 ml) for 16 hours and then left at room temperature for 48 hours. Evaporation afforded a residue which was taken into pyridine (160 ml) and treated with acetic anhydride (19.8 ml). After 24 hours the reaction mixture was diluted with ethyl acetate (500 ml) and washed with dilute HCl. Drying and evaporation afforded an oil which was purified by chromatography (SiO$_2$, isohexane:ethyl acetate, 5:1 as eluant) to afford the subtitle compound (5.34 g).

MS (FAB+RbI): 431, 429 (M+Rb$^+$), 285 (100%).

b) 1,2,3-Tri-O-acetyl-5,6-dideoxy-β-D-ribo-heptofuranuronic acid, ethyl ester

Prepared according to the method of example 8b) using the product of step a).

MS (FAB+RbI): 433, 431 (M+Rb$^+$), 185 (100%).

c) 2,3-Di-O-acetyl-1,5,6-trideoxy-1-[5,7-bis(propylthio)-3H-1,2,3-triazolo[4,5-d]pyrimidin-3-yl]-β-D-ribo-heptofuranuronic acid, ethyl ester and 2,3-di-O-acetyl-1,5,6-trideoxy-1[5,7-bis(propylthio)-2H-1,2,3-triazolo[4,5-d]pyrimidin-2-yl]-β-D-ribo-heptofuranuronic acid, ethyl ester.

The product of step b) (1.00 g) and the product of step 14b) (0.78 g) were mixed with p-toluenesulfonic acid (12 mg) and stirred thoroughly under water pump vacuum. The mixture was plunged into an oil bath at 140°. Heating was continued for 10 mins then the flask cooled and the reaction mixture taken into chloroform. Washing with saturated sodium bicarbonate solution, drying, evaporation and chromatography (SiO$_2$, dichloromethane:ethyl acetate, 15:1 as eluant) gave the subtitle compounds (5.34 g) as an inseparable mixture.

d) 1,5,6-Trideoxy-1-[5,7-bis(propylthio)-3H-1,2,3-triazolo[4,5-d]pyrimidin-3-yl]-β-D-ribo-heptofuranuronic acid, sodium salt Prepared according to the method of example 3c) using the product of step c).

MS (FAB+RbI) 433, 431 (M+Rb$^+$).

Pharmaceutical Compositions

The novel compounds of the present invention may be administered parenterally, intravenously, by inhalation, or orally. A preferred route of administration is intravenous infusion.

The dosage will depend on the route of administration, the severity of the disease, age and weight of the patient, as well as other factors normally considered by the attending physician, when determining the individual regimen and dosage level as the most appropriate for a particular patient.

Examples of pharmaceutical compositions which may be used, and suitable adjuvants, diluents or carriers, are as follows:

for intravenous injection or infusion—purified water or saline solution;

for inhalation compositions—coarse lactose;

for tablets, capsules and dragees—microcrystalline cellulose, calcium phosphate, diatomaceous earth, a sugar such as lactose, dextrose or mannitol, talc, stearic acid, starch, sodium bicarbonate, and/or gelatin;

for suppositories—natural or hardened oils or waxes.

When a compound according to the present invention is to be used in aqueous solution, e.g. for infusion, it may be necessary to incorporate other excipients. In particular there may be mentioned chelating or sequestering agents, antioxidants, tonicity adjusting agents, pH-modifying agents and buffering agents. Solutions containing a compound of the formula (I) may, if desired, be evaporated, e.g. by freeze-drying or spray-drying, to give a solid composition which may be reconstituted prior to use. The compositions may also comprise suitable preserving, stabilising and wetting agents, solubilisers, e.g. water-soluble cellulose polymer such as hydroxypropyl methylcellulose, or a water-soluble glycol such as propylene glycol, sweetening and colouring agents and flavourings. Where appropriate, the compounds may be formulated in sustained release form.

According to a further aspect of the invention, there is provided the use of a compound according to the formula (I) or a pharmaceutically acceptable salt thereof, for the manufacture of a medicament for the treatment of platelet aggregation disorders.

According to still a further aspect of the invention, there is provided a method for the treatment of any disorder where platelet aggregation is involved, whereby an effective amount of a compound according to the formula (I) is administered to a patient suffering from said disorder.

Pharmaceutically acceptable salts of the compounds of the formula (I) include alkali metal salts, e.g. sodium and potassium salts; alkaline earth metal salts, e.g. calcium and magnesium salts; salts of the group III elements, e.g. aluminium salts; and ammonium salts. Salts with suitable organic bases, e.g. salts with hydroxylamine; lower alkylamines, e.g. methylamine or ethylamine; with substituted lower alkylamines, e.g. hydroxysubstituted alkylamines; or with monocyclic nitrogen heterocyclic compounds, e.g. piperidine or morpholine; and salts with amino acids, e.g. with arginine, lysine etc., or an N-alkyl derivative thereof; or with an aminosugar, e.g. N-methyl-D-glucamine or glucosamine. The just mentioned salts are only examples of salts which may be used in accordance with the present invention, and the list is not in any way to be construed as exhaustive.

Preferred pharmaceutically acceptable salts of the compounds of the formula (I) are alkali metal salts and ammonium salts, more preferably sodium salts and monoammonium salts.

Biological Evaluation

The potency of the compounds of the present invention to act as inhibitors of platelet aggregation was determined from their ability to act as P$_{2T}$ receptor antagonists, as illustrated in the following screen:

Quantification of P$_{2T}$ receptor agonist/antagonist activity in washed human platelets.

Preparation

Human venous blood (100 ml) was divided equally between 3 tubes, each containing 3.2% trisodium citrate (4 ml) as anti-coagulant. The tubes were centrifuged for 15 min at 240G to obtain a platelet-rich plasma (PRP) to which 300 ng/ml prostacyclin was added to stabilize the platelets during the washing procedure. Red cell free PRP was obtained by centrifugation for 10 min at 125G followed by further centrifugation for 15 min at 640G. The supernatant was discarded and the platelet pellet resuspended in modified, calcium free, Tyrode solution (10 ml) CFT, composition: NaCl 137 mM, $NaHCO_3$ 11.9 mM, $NaH_2PO_4$ 0.4 mM, KCl 2.7 mM, $MgCl_2$ 1.1 mM, dextrose 5.6 mM, gassed with 95% $O_2$/5% $CO_2$ and maintained at 37°. Following addition of a further 300 ng/ml $PGI_2$, the pooled suspension was centrifuged once more for 15 min at 640G. The supernatant was discarded and the platelets resuspended initially in 10 ml CFT with further CFT added to adjust the final platelet count to $2 \times 10^5$/ml. This final suspension was stored in a 60 ml syringe at 3° with air excluded. To allow recovery from $PGI_2$-inhibition of normal function, platelets were used in aggregation studies no sooner than 2 hours after final resuspension.

In all studies, 3 ml aliquots of platelet suspension were added to tubes containing $CaCl_2$ solution (60 µl of 50 mM soln, final conc. 1 mM). Human fibrinogen (Sigma, F 4883) and 8-sulphophenyltheophylline (8-SPT, to block any $P_1$ agonist activity of compounds) were added to give final concentrations of 0.2 mg/ml (60 µl of 10 mg/ml solution of clottable protein in saline) and 300 nM (10 µl of 15 mM solution in 6% glucose), respectively. Platelets or buffer as appropriate were added in a volume of 150 µl to the individual wells of a 96 well plate. All measurements were made in triplicate in platelets from each donor.

Protocol a) Assessment of agonist/antagonist potency

Aggregation responses in 96 well plates were measured using the change in absorbance given by the plate reader at 660 nm.

The absorbance of each well in the plate was read at 660 nm to establish a baseline figure. Saline or the appropriate solution of test compound was added to each well in a volume of 10 µl to give a final concentration of 0, 0.01, 0.1, 1, 10 or 100 mM. The plate was then shaken for 5 min on an orbital shaker on setting 10 and the absorbance read at 660 nm. Aggregation at this point was indicative of agonist activity of the test compound. Saline or ADP (30 mM; 10 µl of 450 mM) was then added to each well and the plate shaken for a further 5 min before reading the absorbance again at 660 nm.

Antagonist potency was estimated as % inhibition of the control ADP response. The compounds of the present invention exhibited anti-aggregatory activity when tested as described above.

We claim:

1. A compound of the formula (I)

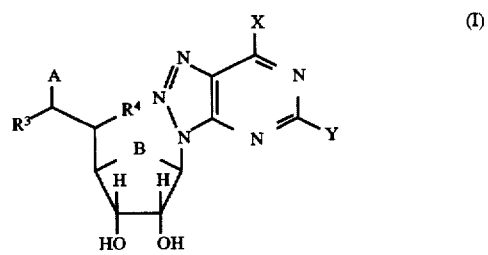

wherein

B is O or $CH_2$;

X is selected from $NR^1R^2$, $SR^1$, and $C_1$–$C_7$ alkyl;

Y is selected from $SR^1$, $NR^1R^2$, and $C_1$–$C_7$ alkyl;

$R^1$ and $R^2$ is each and independently selected from H, or $C_1$–$C_7$ alkyl where one methylene within the chain may optionally be replaced by O, S or NH, and in which the alkyl chain may be optionally substituted by one or more of OH, SH, $NH_2$ or halogen;

$R^3$ and $R^4$ are both H, or $R^3$ and $R^4$ together form a bond;

A is COOH, $C(O)NH(CH_2)_p COOH$, $C(O)N[(CH_2)_q COOH]_2$, $C(O)NHCH(COOH)(CH_2)_r COOH$, or 5-tetrazolyl, wherein p, q and r is each and independently 1, 2 or 3;

as well as pharmaceutically acceptable salts and prodrugs thereof.

2. A compound of the formula (I) according to claim 1, wherein

X is $NR^1R^2$;

Y is $SR^1$;

A is $C(O)NHCH(COOH)(CH_2)_r COOH$; and wherein $R^1$, $R^2$, and r are as defined in claim 1.

3. A compound according to claim 1, wherein

X is $NR^1R^2$ wherein $R^1$ is hydrogen and $R^2$ is as defined in claim 1;

Y is $SR^1$ where $R^1$ is $C_1$–$C_5$ alkyl optionally substituted by one or more halogens; and A is $C(O)NHCH(COOH)(CH_2)COOH$.

4. A compound of formula (I) which is

[1R-(1α(E),2β,3β,4α)]-3-[4-[7-(Butylamino)-5-(propylthio)-3H-1,2,3-triazolo[4,5-d]pyrimidin-3-yl]-2,3-dihydroxycyclopentyl]-2-propenoic acid, sodium salt;

[1R-(1α(E),2β,3β,4α)]-N-[3-[4-[7-(Butylamino)-5-(propylthio)-3 H-1,2,3-triazolo[4,5-d]pyrimidin-3-yl]-2,3-dihydroxycyclopentyl]-2-propenoyl]-L-aspartic acid, disodium salt;

[1S-(1α,2β,3β,4α)]-4-[7-(Butylamino)-5-(propylthio)-3H-1,2,3-triazolo-[4,5-d]pyrimidin-3-yl]-2,3-dihydroxycyclopentanepropanoic acid, sodium salt;

[1R-(1α(E),2β,3β,4α)]-3-[4-[7-(Butylamino)-5-(pentylthio)-3H-1,2, 3-triazolo[4,5-d]pyrimidin-3-yl]-2,3dihydroxycyclopentyl]-2-propenoic acid, sodium salt;

[1R-(1α(E),2β,3β, 4α)]-3-[4-[7-(Ethylamino)-5-(pentylthio)-3H-1,2,3-triazolo[4,5-d]pyrimidin-3-yl]-2,3-dihydroxycyclopentyl]-2-propenoic acid, sodium salt;

[1S-(1α,2β,3β,4α)]-4-[7-(Butylamino)-5-(pentylthio)-3H-1,2,3-triazolo[4,5-d]pyrimidin-3-yl]-2,3dihydroxy-cyclopentanepropanoic acid, sodium salt;

[1S-(1α,2β,3β,4α)]-4-[7-(Ethylamino)-5-(pentylthio)-3H-1,2,3-triazolo[4,5-d]pyrimidin-3-yl]-2,3 dihydroxy-cyclopentanepropanoic acid, sodium salt;

[1R-(1α,2α,3β,5β)]-3-[7-(Butylamino)-5-(propylthio)-3H-1,2,3-triazolo-[4,5-d]pyrimidin-3-yl]-5-[2-(1H-tetrazol-5-yl)ethyl]-1,2-cyclopentanediol;

[1R-(1α,2β,3β,4α)]-N-[3-[4-[7-(Butylamino)-5-(propylthio)-3H-1,2,3-triazolo[4,5-d]pyrimidin-3-yl]-2,3-dihydroxycyclopentyl]propanoyl]-L-aspartic acid;

[1R-(1α(E),2β,3β,4α)]-N-[3-[4-[7-(Hexylamino)-5-(propylthio)-3H-1,2,3-triazolo[4, 5-d]pyrimidin-3-yl]-2,3-dihydroxycyclopentyl]-2-propenoyl]-L-aspartic acid;

[1R-(1α(E),2β,3β,4α)]-3-[4-[7-(3,3-Dimethylbutylamino)-5-(propylthio)-3H-1,2,3-triazolo[4,5-d]pyrimidin-3-yl]-2,3-dihydroxycyclopentyl]-2-propenoic acid;

[1R-(1α(E),2β,3β,4α)]-3-[4-[7-(2-Methoxy)ethylamino)-5-(propylthio)-3H-1,2, 3-triazolo[4,5-d]pyrimidin-3-yl]-2,3-dihydroxycyclopentyl]-2-propenoic acid;

[1R-(1α, 2β,3β,4α)]-N-[3-[4-[7-(Hexylamino)-5-(propylthio)-3H-1,2,3-triazolo[4,5-d]pyrimidin-3-yl]-2,3-dihydroxycyclopentylpropanoyl]-L-aspartic acid;

[1R-(1α(E),2β,3β,4α)]-N-[3-[4-[5-[(3,3,3-Trifluoropropyl)thiol-7-[2-(methylthio) ethylamino]-3H-1,2,3triazolo[4,5-d]pyrimidin-3-yl]-2,3-dihydroxycyclopentyl]-2-propenoyl]-L-aspartic acid, monoammonium salt;

(E)-1-[7-(Butylamino)-5-(propylthio)-3H-1,2,3-triazolo[4,5-d]pyrimidin-3-yl]-1,5,6-trideoxy-β-D-ribo-hept-5-enofuranuronic acid;

(E)-N-[1-[7-(Butylamino)-5-(propylthio)-3H-1,2,3yl]-triazolo[4,5-d]pyrimidin-3-yl]-1,5,6-trideoxy-β-D-ribo-hept-5-enofuranuronoyl]-L-aspartic acid;

(E)-N-[1-[7-Amino-5-(propylthio)-3H-1,²,3-triazolo[4,5-d]pyrimidin-3-yl]-1,5,6-trideoxy-β-D-ribo-hept-5-enofuranuronoyl]-L-aspartic acid, monoammonium salt;

(E)-N-[1-[7-(Butylamino)-5-(propylthio)-3H-1,2,3-triazolo[4,5-d]pyrimidin-3-yl]-1,5,6-trideoxy-β-D-ribo-heptofuranuronoyl]-L-aspartic acid, monoammonium salt;

(E)-N-[1,5,6-Trideoxy-1-[7-(hexylamino)-5-(propylthio)-3H-1,2,3-triazolo-[4,5-d]pyrimidin-3-yl]-β-D-ribo-hept-5-enofuranuronoyl]-L-aspartic acid, monoammonium salt;

(E)-1-[7-(N-Butyl-N-methyl-amino)-5-(propylthio)-3H-1,2,3-triazolo[4,5-d]-pyrimidin-3-yl]-1,5,6-trideoxy-β-D-ribo-hept-5-enofuranuronic acid;

(E)-N-[1-[7-(Butylamino)-5-(methylthio)-3H-1,2,3-triazolo[4,5-d]pyrimidin-3-yl]-1,5,6-trideoxy-β-D-ribo-hept-5-enofuranuronoyl]-L-aspartic acid;

(E)-1-[5-Butyl-7-(butylamino)-3H-1,2,3-triazolo[4,5-d]pyrimidin-3-yl]-1,5,6-trideoxy-β-D-ribo-hept-5-enofuranuronic acid;

(E)-1-[7-Butyl-5-(propylthio)-3H-1,2,3-triazolo[4,5-d]pyrimidin-3-yl]-1,5,6trideoxy-β-D-ribo-hept-5-enofuranuronic acid;

(E)-N-[1-[5,7-Di(butylamino)-3H-1,2,3-triazolo[4,5-d]pyrimidin-3-yl]-1,5,6-trideoxy-β-D-ribo-heptofuranuronoyl]-L-aspartic acid, monoammonium salt;

(Z)-1-[7-(Butylamino)-5-(propylthio)-3H-1,2,3-triazolo[4,5-d]pyrimidin-3-yl]-1,5,6-trideoxy-β-D-ribo-hept-5-enofuranuronic acid;

N-Butyl-5-(propylthio)-3-[5,6-dideoxy-6-(1H-tetrazol-5-yl)-β-D-ribo-hexofuranosyl]-3H-1,2,3-triazolo[4,5-d]pyrimidine-7-amine; or 1,5,6-Trideoxy-1-[5,7-bis(propylthio)-3H-1,2,3-triazolo[4,5-d]pyrimidin-3-yl]-β-D-ribo-heptofuranuronic acid, sodium salt.

5. A compound of formula (I) which is
(E)-N-[1-[7-(Butylamino)-5-(propylthio)-3H-1,2,3-triazolo[4,5-d]pyrimidin-3-yl]-1,5,6-trideoxy-β-D-ribo-hept-5-enofuranuronoyl]-L-aspartic acid.

6. A compound of formula (I) which is
[1R-(1α,2β,3β,4α)]-N-[3-[4-[7-(Butylamino)-5-(propylthio)-3H-1,2,3-triazolo [4,5-d]pyrimidin-3-yl]-2,3-dihydroxycyclopentyl]propanoyl]-L-aspartic acid.

7. A compound of formula (I) which is
[1R-(1α(E),2β,3β,4α)]-N-[3-[4-[7-(Hexylamino)-5-(propylthio)-3H-1,2,3-triazolo[4,5,-d]pyrimidin-3-yl]-2,3-dihydroxycyclopentyl]-2-propenoyl]-L-aspartic acid.

8. A compound according to claim 4, which compound is
[1R-(1α(E),2β,3β,4α)]-N-[3-[4-[5-[(3,3,3-Trifluoropropyl)thio]-7-[2-(methylthio)ethylamino]-3H-1,2,3-triazolo[4-[5-d]pyrimidin-3-yl]-2,3-dihydroxycyclopentyl]-2-propenoyl3-L-aspartic acid, monoammonium salt.

9. A compound according to formula (I) of claim 1 in salt form.

10. A compound according to claim 9, the compound being an alkali metal salt or an ammonium salt of a compound of the formula (I).

11. A compound according to claim 10, the compound being a sodium salt of a compound of the formula (I).

12. A compound according to claim 10, the compound being a monoammonium salt of a compound of the formula (I).

13. A pharmaceutical composition comprising a compound of the formula (I) according to claim 1 as an active ingredient, together with a pharmaceutically acceptable carrier.

14. A process for the preparation of a compound of the formula (I) according to claim 1, comprising reacting:
(i) a compound of the formula (I) wherein
X is $SR^1$, $NR^1R^2$, or $C_1$–$C_7$ alkyl;
Y is $SR^1$, $NR^1R^2$, $C_1$–$C_7$ alkyl;
$R^1$ and $R^2$ are as defined in formula (I);
B is O or $CH_2$;
$R^3$ and $R^4$ are hydrogen or together form a bond; and
A is COOH;
with a compound having the structure $NH_2(CH_2)_pCOOR^{11}$, $NH[(CH_2)_qCOOR^{11}]_2$, or $NH_2CH(COOR^{11})(CH_2)_rCOOR^{11}$, wherein p, q and r are 1, 2 or 3, and $R^{11}$ is a lower (ar)alkyl;
using methods as employed in peptide synthesis, giving a compound of the formula (I) wherein
X is $SR^1$, $NR^1R^2$, or $C_1$–$C_7$ alkyl;
Y is $SR^1$, $NR^1R^2$, $C_1$–$C_7$ alkyl;
$R^1$ and $R^2$ are as defined in formula (I);
B is O or $CH_2$;
$R^3$ and $R^4$ are hydrogen or together form a bond; and
A is $C(O)NH(CH_2)_pCOOR^{11}$, $C(O)N[(CH_2)_qCOOR^{11}]_2$, or $C(O)NHCH(COOR^{11})(CH_2)_rCOOR^{11}$ where p, q and r are 1, 2 or 3, and $R^{11}$ is a lower (ar)alkyl;
(ii) the product of formula (I) of step (i) is de-esterified, giving a compound of the formula (I) wherein
B is O or $CH_2$;
X is $NR^1R^2$, $SR^1$, or $C_1$–$C_7$ alkyl Y is $SR^1$, $NR^1R^2$, or $C_1-C_7$ alkyl;

$R^1$ and $R^2$ is each and independently H, or $C_1-C_7$ alkyl optionally substituted upon or within the alkyl chain by one or more of O, S, N or halogen;

$R^3$ and $R^4$ are both H, or $R^3$ and $R^4$ together form a bond; and

A is $C(O)NH(CH_2)_pCOOH$, $C(O)N[(CH_2)_qCOOH]_2$, or $C(O)NHCH(COOH)(CH_2)_rCOOH$, wherein p, q and r is each and independently 1, 2 or 3.

15. A method for the treatment of platelet aggregation disorders, whereby an effective amount of a compound of the formula (I) according to claim 1 is administered to a subject suffering from said platelet aggregation disorder.

16. A method according to claim 15, wherein the platelet aggregation disorder is unstable angina.

17. A method according to claim 15, wherein the platelet aggregation disorder is coronary angioplasty.

18. A method according to claim 15, wherein the platelet aggregation disorder is myocardial infarction.

19. A compound of the formula (I)

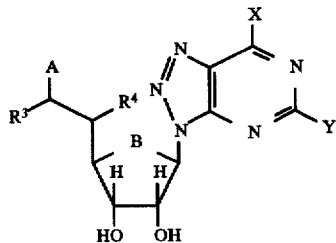

(I)

wherein

B is O or $CH_2$;

X is selected from $NR^1R^2$, $SR^1$, and $C_1-C_7$ alkyl;

Y is selected from $SR^1$, $NR^1R^2$, and $C_1-C_7$ alkyl;

$R^1$ and $R^2$ is each and independently selected from H, or $C_1-C_7$ alkyl, where one methylene within the chain may optionally be replaced by O, S or NH, and in which the alkyl chain may be optionally substituted by one or more of OH, SH, $NH_2$ or halogen;

$R^3$ and $R^4$ are both H, or $R^3$ and $R^4$ together form a bond;

A is selected from $COOR^{11}$, $C(O)NH(CH_2)_pCOOR^{11}$, $C(O)N[CH_2)_qCOOR^{11}]_2$, and $C(O)NHCH(COOR^{11})(CH_2)_rCOOR^{11}$, wherein p, q and r is 1, 2, or 3, and $R^{11}$ is a lower alkyl of 1 to 4 carbon atoms or lower aralkyl containing 1 to 4 carbon atoms in the alkyl portion;

as well as pharmaceutically acceptable salts and prodrugs thereof.

* * * * *